United States Patent [19]

Ho et al.

[11] Patent Number: 4,990,275
[45] Date of Patent: Feb. 5, 1991

[54] POLYIMIDE ALIPHATIC POLYESTER COPOLYMERS (C-2356)

[75] Inventors: W. S. Winston Ho; Guido Sartori, both of Annandale; Warren A. Thaler, Flemington; David C. Dalrymple, Bloomsbury, all of N.J.

[73] Assignee: Exxon Research and Engineering Company, Florham Park, N.J.

[21] Appl. No.: 519,526

[22] Filed: May 4, 1990

Related U.S. Application Data

[62] Division of Ser. No. 422,385, Oct. 16, 1989, Pat. No. 4,944,880.

[51] Int. Cl.$^5$ .............................. B01D 69/00
[52] U.S. Cl. .................. 252/62.3 Q; 210/500.39
[58] Field of Search .............. 252/60, 62.3, 62.3 Q, 252/510, 511, 378 R, 190, 184; 210/500.1, 500.21, 500.27, 500.28, 500.33, 500.39, 500.35; 55/16, 158

[56] References Cited

U.S. PATENT DOCUMENTS

| | | | |
|---|---|---|---|
| 2,930,754 | 3/1960 | Stuckey | 210/23 |
| 2,958,656 | 11/1960 | Stuckey | 210/23 |
| 3,370,102 | 2/1968 | Carpenter et al. | 260/674 |
| 4,115,465 | 9/1978 | Elfert et al. | 260/674 |
| 4,233,435 | 11/1980 | Boldebuck et al. | 528/350 |
| 4,307,226 | 12/1981 | Bolon et al. | 528/288 |
| 4,766,229 | 8/1988 | Kobayashi et al. | 252/184 |
| 4,775,586 | 10/1988 | Bohrn et al. | 252/378 R |
| 4,818,255 | 4/1989 | Matsuura et al. | 252/190 |
| 4,847,333 | 7/1989 | Lubowitz et al. | 252/511 |
| 4,929,358 | 5/1990 | Koenitzer | 210/640 |

FOREIGN PATENT DOCUMENTS

| | | |
|---|---|---|
| 56014528 | 7/1979 | Japan . |
| 56036192 | 8/1979 | Japan . |
| 56036561 | 8/1979 | Japan . |
| 56062823 | 10/1979 | Japan . |
| 56076591 | 11/1979 | Japan . |
| 57094024 | 12/1980 | Japan . |

Primary Examiner—Frank Sever
Attorney, Agent, or Firm—Ronald D. Hantman

[57] ABSTRACT

A new copolymer composition comprising the hard segment of a polyimide and the soft segment of an oligomeric aliphatic polyester. The new polyimide copolymer membranes have exhibited high thermal stability for separation of an aromatic/saturate mixture. These new membranes have higher aromatic/saturate selectivity than polyurethanes.

15 Claims, 28 Drawing Sheets

POLYIMIDE ALIPHATIC POLYESTER COPOLYMERS (C-2356)

This is a division of application Serial No. 422,385, filed Oct. 16, 1989, now Pat. 4,944,880.

BACKGROUND

The present invention relates to a new composition of matter for the separation of aromatics from saturates.

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e., aromatic, unsaturated, saturated, by permeating a portion of the mixture through a non-porous cellulose ether membrane and removing permeate from the permeate side of the membrane using a sweep gas or liquid. Feeds include hydrocarbon mixtures, e.g., naphtha (including virgin naphtha, naphtha from thermal or catalytic cracking, etc.).

U.S. Pat. No. 2,930,754 teaches a method for separating hydrocarbons, e.g., aromatic and/or olefins from gasoline boiling range mixtures, by the selective permeation of the aromatic through certain non-porous cellulose ester membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation.

Compared to distillation, membrane permeation can lead to considerable energy savings. A membrane can separate a mixture of aromatics and saturates, e.g., a heavy cat naphtha, into a high-octane, mainly aromatic permeate and a high-cetane, mainly saturated retentate. Both permeate and retentate are more valuable than the starting heavy cat naphtha.

SUMMARY OF THE INVENTION

The present invention is a new composition of matter and its use in a process for separating aromatics from feeds which are mixtures of aromatics and non-aromatics. The composition of matter includes a hard segment having a glass transition temperature (Tg) of greater than 130.C and a soft segment having a Tg less than the Tg of the hard segment. The composition is formed into a membrane which includes a copolymer composition with the hard segment of a polyimide and the soft segment of an oligomeric aliphatic polyester, wherein the hard and soft segments are alternating, the polyimide is derived from a dianhydride and a diamine, and the oligomeric aliphatic polyester is a polyadipate, a polysuccinate, a polymalonate, a polyoxalate or a polyglutarate.

In a preferred embodiment, the dianhydride has between 8 and 20 carbons, the diamine has between 2 and 30 carbons, and the oligomeric aliphatic polyester is a polyadipate or a polysuccinate.

DESCRIPTION OF THE PREFERRED EMBODIMENT

The present invention is new polyimide copolymers for membranes to separate aromatics from feed streams of aromatics and non-aromatics. The copolymer contains alternating hard and soft segments.

Figure 1:
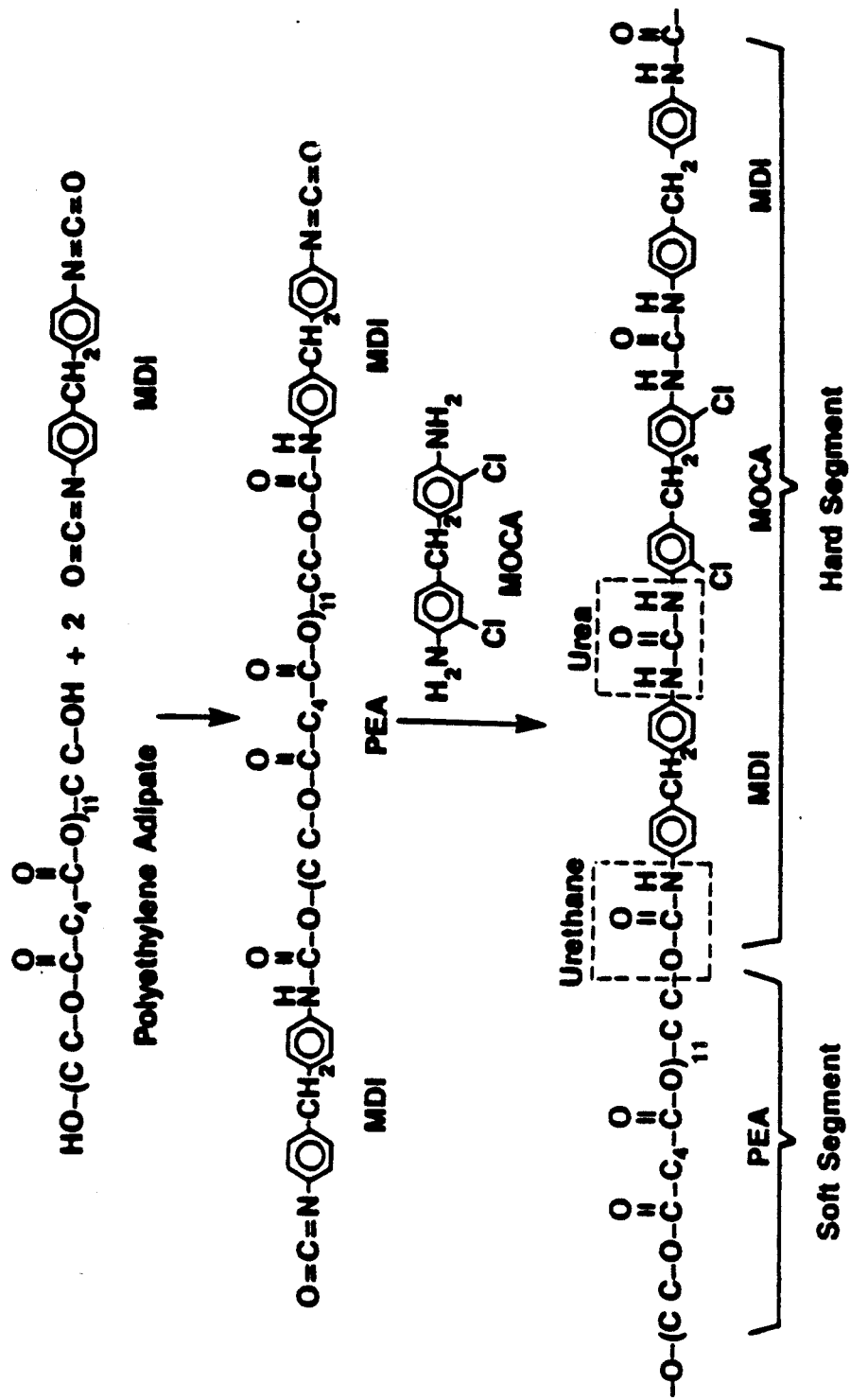
FIG. 1 shows the synthesis and composition of the copolymer containing the hard segment of the polyurea/urethane with 2 chlorines and the soft segment of polyethylene adipate with a molecular weight of 2000 (PEA 2000).

We have synthesized a copolymer containing the hard segment of the polyurea/urethane with 2 chlorines and the soft segment of the polyethylene adipate with a molecular weight of 2000 (PEA 2000). The hard and soft segments are alternating in the copolymer. FIG. 1 shows the synthesis and composition of the copolymer. In the synthesis, one mole of polyethylene adipate diol reacts with 2 moles of methylene diphenylisocyanate (MDI). That is, polyethylene adipate abbreviated as PEA is end-capped with MDI to make a pre-polymer. This pre-polymer is then chain-extended with di-o-chloroaniline (MOCA) to make the copolymer containing the soft segment of PEA and the hard segment of polyurea/urethane hard segment with 2 chlorines (MDI-MOCA-MDI).

Figure 2:
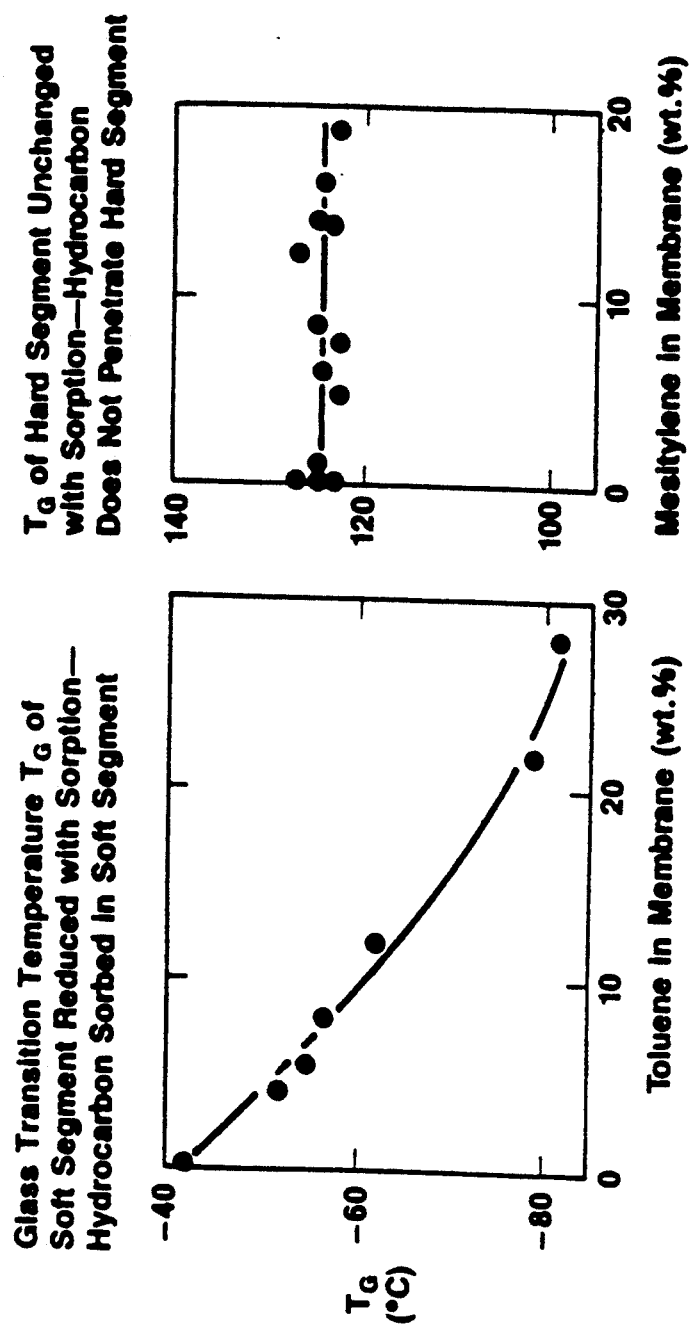
FIG. 2A and 2B show that the soft segment of the polyurethane controls sorption, i.e., selectivity and permeability.

We have elucidated the function of soft and hard segments for membrane separation. The soft segment governs sorption of hydrocarbons, i.e. selectivity and permeability whereas the hard segment provides the thermal stability of the membrane. We have studied the glass transition temperatures, Tg, of the soft and hard segments of the copolymer shown in FIG. 1. FIG. 2A shows Tg results for the soft segment. The Tg of the soft segment is reduced with the sorption of toluene in the polyurethane membrane. This means that the hydrocarbon is sorbed in the soft segment. FIG. 2B shows Tg results for the hard segment. The Tg of the hard segment is unchanged with the sorption of mesitylene in the membrane. This means that the hydrocarbon does not penetrate the hard segment. Mesitylene instead of toluene was used in the Tg experiments since the Tg of the hard segment is higher than the boiling point of toluene. As shown in these diagrams, the hard segment has a much higher Tg than the soft segment. These Tg results show that the soft segment governs sorption. That is, the soft segment governs selectivity and permeability.

Table 1 shows that the hard segment provides the thermal stability of the membrane. This table gives two evidences to support this conclusion. The first evidence is that a chlorinated hard segment gives a better membrane stability than a hard segment without chlorine. The chlorinated hard segment from MDI and MOCA gives a membrane stability of 150° C. However, the hard segment without chlorine, which is from MDI and methylene dianiline, results in a membrane stability of only 100° C. Both membranes have the same soft segment of polyethylene adipate with a molecular weight of 2000. The chlorinated hard segment has a higher glass transition temperature than the hard segment without chlorine. The enhanced membrane stability and higher glass transition temperature for the chlorinated hard segment are presumably due to the dipole-dipole interaction of the chlorine groups. The second evidence is that crosslinking of hard segment improves the thermal stability of the membrane. As shown in the lower part of this table, the hard segment is from toluene diisocyanate (TDI) and phenylene diamine. Crosslinking of the hard segment is via the use of 1,1,1-trimethylol-ethane to replace 25 mole % of phenylene diamine in the hard segment. The crosslinked hard segment gives a better membrane stability than the hard segment without crosslinking. Both membranes have the same soft segment of polydiethyleneglycol adipate with a molecular weight of 2000.

TABLE 1

| HARD SEGMENT OF POLYURETHANE INFLUENCES THERMAL STABILITY | | |
|---|---|---|
| | Membrane Stability (°C.) | Glass Transition Temperature (°C.) |
| Chlorinated Hard Segment Gives Better Stability | | |
| Chlorinated Hard Segment (MDI/MOCA) | 150 | 125 |
| Hard Segment Without Chlorine (MDI/Methylene Dianiline) | 100 | 95 |
| Crosslinking of Hard Segment Improves | | |

TABLE 1-continued

HARD SEGMENT OF POLYURETHANE INFLUENCES THERMAL STABILITY

| | Membrane Stability (°C.) | Glass Transition Temperature (°C.) |
|---|---|---|
| Stability | | |
| Crosslinked Hard Segment (TDI/Phenylene Diamine) | 120 | 125 |
| Hard Segment Without Crosslinking | 80 | — |

Figure 3:
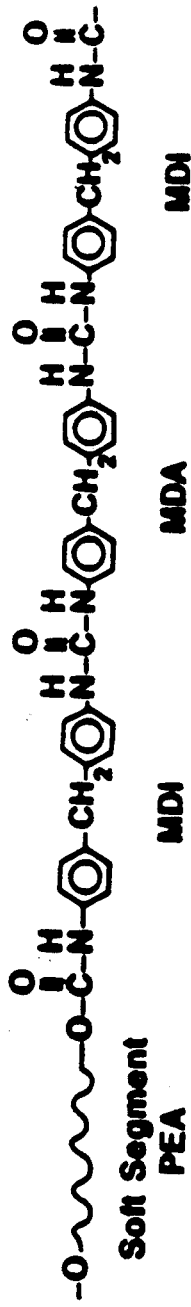
FIG. 3 shows three polyurethanes with different hard segments.
Figure 3:
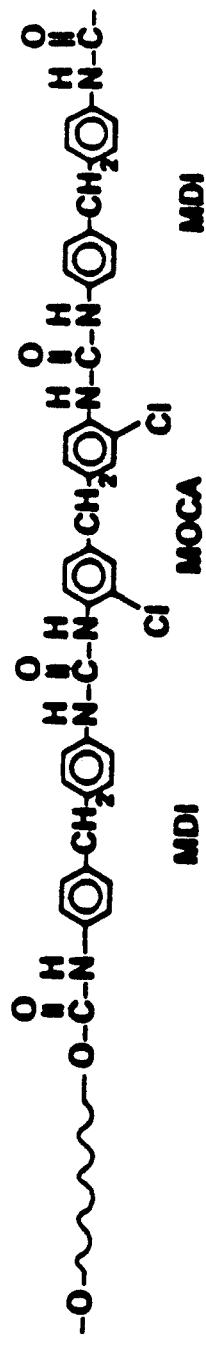
Figure 3:
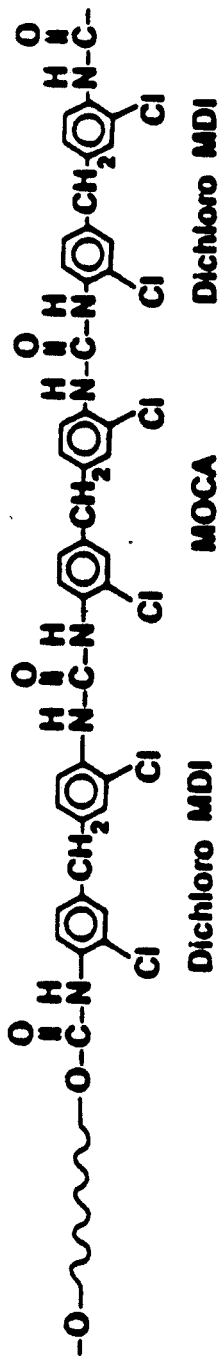

We have also synthesized a copolymer containing the hard segment of the polyurea/urethane with 6 chlorines and the soft segment of polyethylene adipate with a molecular weight of 2000 (PEA 2000) via the synthesis method described above, but using methylene dichlorophenylisocyanate (dichloro MDI) instead of methylene diphenylisocyanate (MDI). FIG. 3 shows the three polyurethanes with the same soft segment but with three different hard segments. The soft segment was the polyethylene adipate (PEA) with a molecular weight of 2000. The first polyurethane had a hard segment without chlorine, which was MDI/methylene dianiline (MDA)/MDI. The second polyurethane had a hard segment with 2 chlorines, which was MDI/MOCA/MDI. The third polyurethane had a hard segment with 6 chlorines, which was dichloro MDI/MOCA/dichloro MDI. This is the advanced polyurethane.

We have evaluated the three polyurethane membranes to separate a mixture containing toluene and isooctane in a pervaporation apparatus. The initial mixture contains about equal weights of the two hydrocarbons. The pervaporation apparatus is a cell separated into two compartments by a porous metal plate, on which the membrane is supported. During a pervaporation experiment the toluene-isooctane mixture is circulated through the upper compartment at the desired temperature. The lower compartment is kept at reduced pressure. The permeate is collected in a trap cooled with dry ice-acetone or isopropanol and periodically analyzed by gas chromatography.

Figure 4:
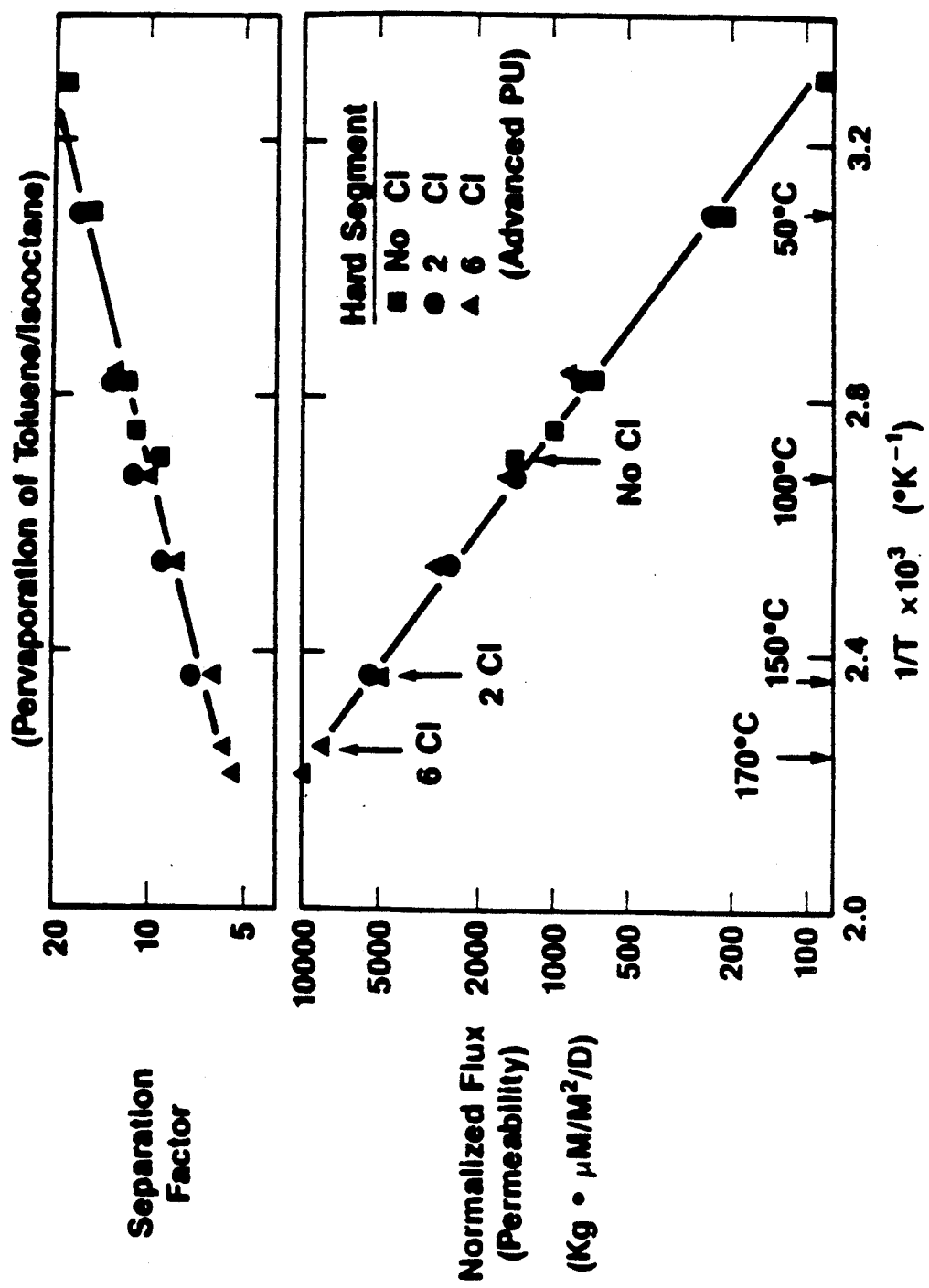
FIG. 4 shows that chlorinated polyurethanes have higher thermal stability than the polyurethane without chlorines, the polyurethane containing the hard segment with 6 chlorines has the highest thermal stability among the three polyurethanes investigated, and change in hard segment does not affect selectivity and permeability.

FIG. 4 compares the performance for these three polyurethane membranes with different hard segments in the pervaporation of the toluene/isooctane feed. In the lower part of this figure, we plot normalized flux, i.e., permeability in the unit of kilogram of permeate per meter square membrane area per day for a normalized membrane thickness of 1 micron ($Kg \cdot \mu M/M^2/D$), as a function of temperature. The hard segment without chlorine gave a membrane stability of 100° C. The hard segment with 2 chlorines resulted in a membrane stability of 150° C. However, the advanced polyurethane containing the hard segment with 6 chlorines had a thermal stability of about 170° C. These results have reinforced our finding that the hard segment provides thermal stability. The advanced polyurethane with the highly chlorinated hard segment had the highest thermal stability among the polyurethanes investigated. This figure shows that the permeability was identical for these three membranes at a given temperature, at which they were stable. This was due to the fact that they had the same soft segment. The upper part of this figure shows that the selectivity was about the same for these three membranes at a given temperature, at which they were stable. This was also due to the fact that they had the same soft segment. Therefore, change in hard segment did not affect selectivity and permeability significantly. These results have reinforced our findings that the soft segment governs selectivity and permeability, and the hard segment provides thermal stability.

Figure 5:
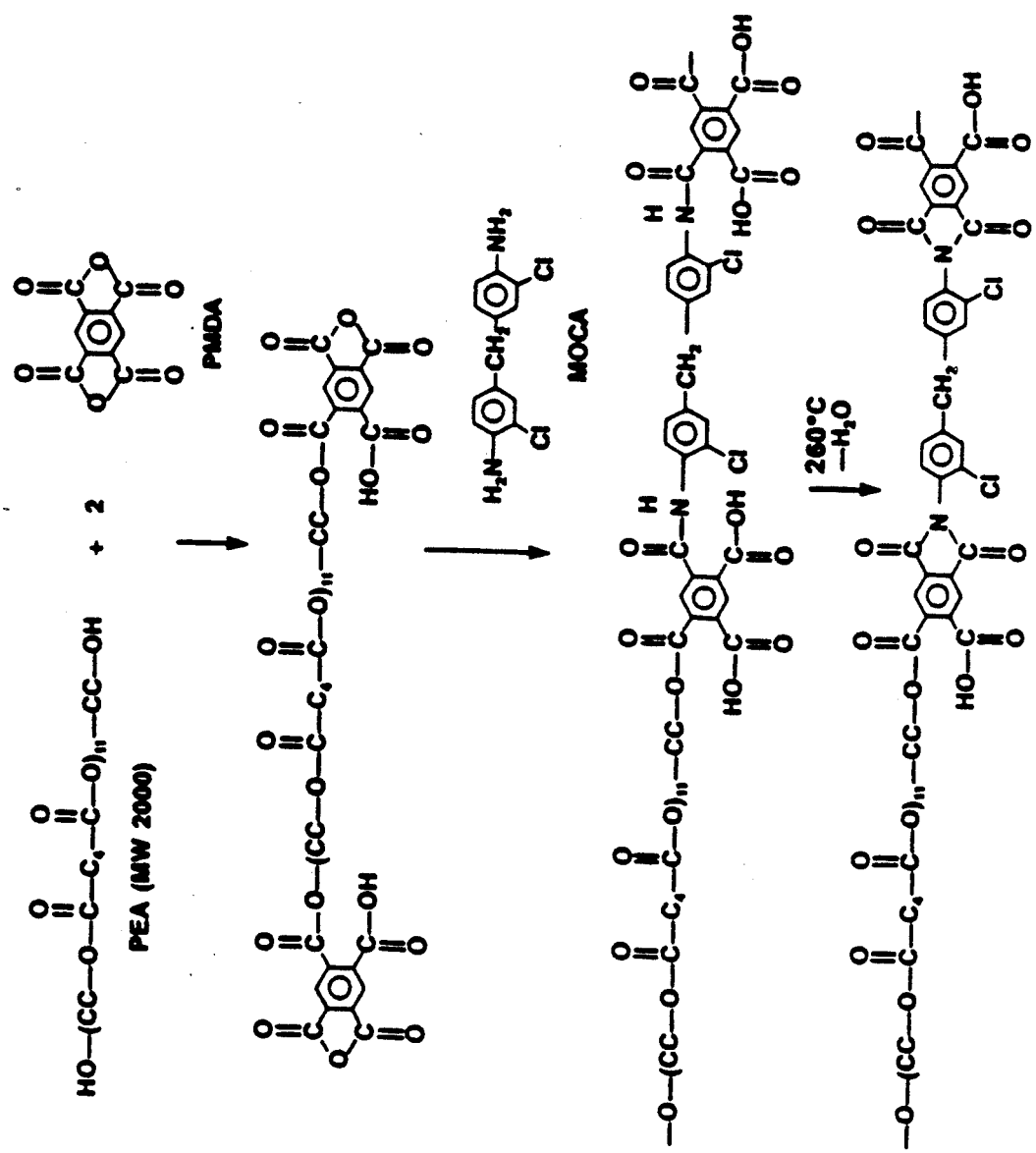
FIG. 5 shows the synthesis and composition of a new copolymer of the present invention containing the hard segment of polyimide derived from pyromellitic dianhydride (PMDA) and methylene di-o-chloroaniline (MOCA) and the soft segment of polyethylene adipate with a molecular weight of 2000 (PEA 2000).

Through our finding that the hard segment provides thermal stability, which is enhanced with increasing hard segment Tg, we have synthesized new copolymers of the present invention containing polyimide with high Tg as the hard segment to improve thermal stability. FIG. 5 shows the synthesis and composition of an example of the new copolymers containing the hard segment of polyimide derived from pyromellitic dianhydride (PMDA) and methylene di-o-chloroaniline (MOCA) and the soft segment of polyethylene adipate with a molecular weight of 2000 (PEA 2000). In the synthesis, one mole of polyethylene adipate (PEA) is reacted with two moles of pyromellitic dianhydride (PMDA) to make pre-polymer in the endcapping step. Then, one mole of the pre-polymer reacts with one mole of methylene di-o-chloroaniline (MOCA) to make a copolymer containing PEA soft segment and polyamic acid hard segment in the chain-extension step. Finally, heating of the copolymer at 260-300° C. for about 0.5 hour leads to the new copolymer containing PEA soft segment and polyimide hard segment. The heating step converts the polyamic acid hard segment to the polyimide hard segment via the imide ring closure with removal of water.

In the synthesis, dimethyl formamide (DMF) is used as solvent in the chain-extension step. DMF is a preferred solvent, but other suitable solvents may be used. This gives a concentrated solution of the polyamic acid/polyadipate copolymer in DMF. The new polyimide copolymer membrane can be prepared by casting the solution on a glass plate or a porous support, adjusting the thickness by means of a casting knife, and drying the membrane first at room temperature to remove most of the solvent, then at 120° C. overnight. The membrane is then removed from the glass plate via soaking in water. Finally, heating of the membrane at 300° C. for about 0.5 hour results in the polyimide copolymer membrane.

The new polyimide copolymer membranes can be used for the separation of aromatics from saturates. In separation experiments similar to those described above, the membranes are employed to separate a feed mixture containing 50 wt% toluene and 50 wt% isooctane or a mixture containing 10 wt% toluene, 40 wt% p-xylene, 20 wt% isooctane, and 30 wt% n-octane in the pervaporation apparatus.

The membranes are useful for the separation of aromatics from saturates in petroleum and chemical streams, and have been found to be particularly useful for the separation of large substituted aromatics from saturates as are encountered in heavy cat naphtha streams. Other streams which are also suitable feed streams for aromatics from saturates separation are intermediate cat naphtha streams boiling at 93-160° C., light aromatics content streams boiling in the $C_5$-150° C. range, light catalytic cycle oil boiling in the 200-345°

C. range as well as streams in chemical plants which contain recoverable quantities of benzene, toluene, xylenes (BTX) or other aromatics in combination with saturates. The separation techniques which may successfully employ the membranes of the present invention include perstraction and pervaporation.

Perstraction involves the selective dissolution of particular components contained in a mixture into the membrane, the diffusion of those components through the membrane and the removal of the diffused components from the downstream side of the membrane by the use of a liquid sweep stream. In the perstractive separation of aromatics from saturates in petroleum or chemical streams (particularly heavy cat naphtha streams) the aromatic molecules present in the feedstream dissolve into the membrane film due to similarities between the membrane solubility parameter and those of the aromatic species in the feed. The aromatics then permeate (diffuse) through the membrane and are swept away by a sweep liquid which is low in aromatic content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids, therefore, would include, for example, $C_3$ to $C_6$ saturated hydrocarbons and lube basestocks ($C_{15}$–$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

Pervaporation, by comparison, is run at generally higher temperatures than perstraction and relies on vacuum on the permeate side to evaporate the permeate from the surface of the membrane and maintain the concentration gradient driving force which drives the separation process. As in perstraction, the aromatic molecules present in the feed dissolve into the membrane film, migrate through said film and merge on the permeate side under the influence of a concentration gradient. Pervaporative separation of aromatics from saturates can be performed at a temperature of about 25° C. for the separation of benzene from hexane but for separation of heavier aromatic/saturate mixtures, such as heavy cat naphtha, higher temperatures of at least 80° C. and higher, preferably at least 100° C. and higher, more preferably 120° C. and higher should be used. Temperatures of about 210° C. have been successfully used with membranes of the present invention, the maximum upper limit being that temperature at which the membrane is physically damaged. Vacuum on the order of 1–50 mm Hg is pulled on the permeate side. The vacuum stream containing the permeate is cooled to condense out the highly aromatic permeate. Condensation temperature should be below the dew point of the permeate at a given vacuum level.

The membrane itself may be in any convenient form utilizing any convenient module design. Thus, sheets of membrane material may be used in spiral wound or plate and frame permeation cell modules. Tubes and hollow fibers of membranes may be used in bundled configurations with either the feed or the sweep liquid (or vacuum) in the internal space of the tube or fiber, the other material obviously being on the other side.

When the membrane is used in a hollow fiber configuration with feed introduced on the exterior side of the fiber, the sweep liquid flows on the inside of the hollow fiber to sweep away the permeated highly aromatic species, thereby maintaining the desired concentration gradient. The sweep liquid, along with the aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering of temperature.

It has been observed that the new polyimide copolymer membranes can separate toluene from isooctane and toluene from n-octane, showing good selectivity and permeability. These membranes have higher toluene/isooctane and toluene/n-octane selectivities than the polyurethane membranes with the same polyadipate soft segment. These membranes have exhibited the highest thermal stability, at least 210° C., among the membranes investigated for pervaporation separation of the feed mixtures described above.

The copolymer composition of the present invention comprises the hard segment of a polyimide and the soft segment of an oligomeric aliphatic polyester. The polyimide is derived from a dianhydride and a diamine, and the oligomeric aliphatic polyester is a polyadipate, a polysuccinate, a polymalonate, a polyoxalate or a polyglutarate.

In a preferred embodiment, the dianhydride has between 8 and 20 carbons and the diamine has between 2 and 30 carbons, and the oligomeric aliphatic polyester is a polyadipate or a polysuccinate. The dianhydride is preferred to be an aromatic compound. Non-limiting examples include pyromellitic dianhydride, 3,3',4,4'-benzophenone tetracarboxylic dianhydride, 4,4'-(hexafluoroisopropylidene)-bis(phthalic anhydride), 4,4'-oxydiphthalic anhydride, diphenylsulfone-3,3',4,4'-tetracarboxylic dianhydride. Non limiting examples of diamine include phenylene diamine, methylene dianiline (MDA), methylene di-o-chloroaniline (MOCA), methylene bis (dichloroaniline) (tetrachloro MDA), methylene dicyclohexylamine ($H_{12}$-MDA), methylene dichlorocyclohexylamine ($H_{12}$-MOCA), methylene bis (dichlorocyclohexylamine) (tetrachloro $H_{12}$-MDA), 4,4'-(hexafluoroisopropylidene)-bisaniline (6F diamine), 3,3'-diaminophenyl sulfone (3,3'DAPSON), 4,4'-diaminophenyl sulfone (4,4'DAPSON), 4,4'-dimethyl-3,3,-diaminophenyl sulfone (4,4'-dimethyl-3,3'DAPSON), 2,4-diamino cumene, methyl bis(di-o-toluidine), oxydianiline (ODA), bisaniline A, bisaniline M, bisaniline P, thiodianiline, 2,2-bis[4-(4-aminophenoxy) phenyl] propane (BAPP), bis[4-(4-aminophenoxy phenyl) sulfone (BAPS), 4,4'-bis(4aminophenoxy) biphenyl (BAPB), 1,4-bis(4-aminophenoxy) benzene (TPE-Q), and 1,3-bis(4-aminophenoxy) benzene (TPE-R).

U.S. Patents 4,233,435 and 4,307,226 (equivalent to GB 2,075,998) to General Electric Company and Japanese Patents 56,014,528; 56,062,823; 56,036,192; 56,036,561; 56,076,591 and 57,094,024 to Nitto Electric Industrial Co., Ltd. are not related to membranes for separation, and they are cited herewith for reference.

U.S. Patent 4,233,435 discloses the production of a polyesterimide resin by reacting a mixture of a diamine, an anhydride, a dihydric alcohol containing 2 esterifiable hydroxyl groups (e.g., ethylene glycol), a polyhydric alcohol containing $\geq$ 3 esterifiable hydroxyl groups (e.g., tris[2-hydroxyethyl] isocyanurate), a lower dialkyl ester of terephthalic and/or isophthalic acid and a monohydric alcohol (e.g., 1-decanol). The resin is used as a coating, e.g., on electrical conductors such as wire.

As disclosed in U.S. 4,307,226 (equivalent to GB 2,075,998), a polyesterimide is mixed with ethylene glycol and heated to incorporate the glycol in the polyesterimide by transesterification so that on cooling a clear homogeneous resin is obtained, which is soluble in a glycol monoether for wire coating applications. The polyesterimide is formed by reacting a mixture of a diamine, an anhydride, an esterifiable dihydric alcohol, a polyhydric alcohol containing $\geq$ 3 esterifiable hydroxyl groups and a di(lower alkyl) terephthalate or isophthalate.

Japanese Patent 56,014,528 discloses the preparation of a polyester or polyesterimide resin for electrically insulating coatings by reacting a mixture of terephthalic acid optionally blended with up to 50 mole % of a polycarboxylic acid, a polyhydric alcohol containing $\geq$ 2 esterifiable hydroxyl groups and optionally a diamine in the presence of at least one esterifying catalyst (e.g. dibutyltin dilaurate).

The reactants used in U.S. Patents 4,233,435 and 4,307,226 and Japanese Patent 56,014,528 do not produce polymers containing the soft segment of an oligomeric aliphatic polyester as disclosed in the present invention. Because the reactants have short chains, it appears that the resulting polymers have reasonably rigid chains with about the same degree of chain flexibility and thus a single glass transition temperature (Tg) for each polymer and do not have hard and soft segments. In addition, the synthesis procedures disclosed in these three patents should result in polyesterimides with random structures since both the esters and alcohols can react with the dianhydrides simultaneously. As disclosed in the present invention, the copolymers synthesized from an oligomeric aliphatic polyester, a dianhydride and a diamine via the sequential end-capping and chain-extension steps contain the hard segment of a polyimide and the soft segment of the oligomeric aliphatic polyester, in which the hard and soft segments are alternating. These copolymers have two Tg values, one for the hard segment domain and the other for the soft segment domain. With the function that the hard segment provides thermal stability and the soft segment governs selectivity and permeability, these copolymers offer superior membrane materials for the separation of the feed mixture containing aromatics and saturates. Thus, the copolymers of the present invention are different from the polymers disclosed in these three patents.

Japanese Patent 56,062,823 discloses the synthesis of a polyesteramide-imide or polyesterimide for use as electric insulating material, adhesive, printed circuit board, lamination material, paint, etc., by modifying a polyester with 1,2,3,4-butanetetracarboxylic acid and an aliphatic polyamine containing $\geq$ 2 amino groups. As disclosed in Japanese Patent 56,036,192, a polyesteramide-imide or polyesterimide is used for printed circuit board. Japanese Patent 56,036,561 discloses the use of a polyesteramide-imide or polyesterimide for heat resistant adhesive. Japanese Patent 56,076,591 claims the use of a polyesteramide-imide or polyesterimide for the insulating material for circuit board. As claimed in Japanese Patent 57,094,024, a polyesteramide-imide or polyesterimide is employed in the laminate board manufacture. As disclosed in these five Japanese patents, both 1,2,3,4-butanetetracarboxylic acid and an aliphatic polyamine are used in the modification of a polyester. Since both the acid and the ester functionality (ester linkage) of the polyester can react with the polyamine simultaneously, the resulting polyesteramide-imide or polyesterimide should have a random structure. Thus, the copolymers of the present invention containing the alternating polyimide hard segments and oligomeric aliphatic polyester soft segments, which are synthesized from an oligomeric aliphatic polyester diol, a dianhydride and a diamine, are different from the polyesteramide-imides or polyesterimides disclosed in these five Japanese patents.

The invention is illustrated further by the following examples, which, however, are not to be taken as limiting in any respect. All parts and percentages, unless expressly stated to be otherwise, are by weight.

EXAMPLE 1

Synthesis of the Polyimide Copolymer Containing the Polyethylene Adipate Soft Segment with a Molecular Weight of 2000

To 10 g (0.005 mole) of polyethylene adipate diol with a molecular weight of 2000 (PEA 2000) heated (about 80° C.) under $N_2$ in a reactor was added 2.18 g (0.01 mole) of pyromellitic dianhydride (PMDA) with stirring. The temperature was increased to about 100° C., and the stirring continued for about 4 hours to complete the end-capping step. To the reactor content was added 5 g of N,N-dimethyl formamide (DMF), and the temperature was dropped to about 80° C. with stirring for about 0.5 hour. To this reactor content was added 1.34 g (0.005 mole) methylene di-o-chloroaniline (MOCA) in 3 g DMF solution dropwise. Until a very viscous solution resulted, which indicated the chain-extension reaction, additional DMF, about 38 g, was added, and the solution was then cooled to room temperature. The resulting solution containing the copolymer with the polyamic acid hard segment and the polyethylene adipate soft segment had suitable consistency for solution casting in the preparation of membranes.

The resulting solution was centrifuged for about 5 minutes. Following centrifugation, a membrane was knife-cast onto a glass plate with a knife gap setting of 13 mils. DMF was allowed to evaporate from the membrane in a hood at ambient conditions over a period of about 17 hours. The membrane was then dried in an oven at 120° C. overnight. The membrane was then removed from the glass plate by soaking it in a water bath. Finally, the membrane was cured, by heating it from room temperature to 300° C., maintaining it at this temperature for about 0.5 hour and then cooling it to room temperature in the curing step, to obtain the polyimide copolymer membrane with the PEA soft segment. The resulting membrane had a thickness of about 94 microns and a polyimide/polyadipate weight ratio of 25/75. The curing step converted the polyamic acid hard segment to the polyimide hard segment via the imide ring closure with removal of water. The polyimide copolymer was insoluble in DMF.

EXAMPLE 2

Pervaporation Results for the Polyimide Copolymer Membrane Containing the Polyethylene Adipate Soft Segment With a Molecular Weight of 2000

Figure 6:
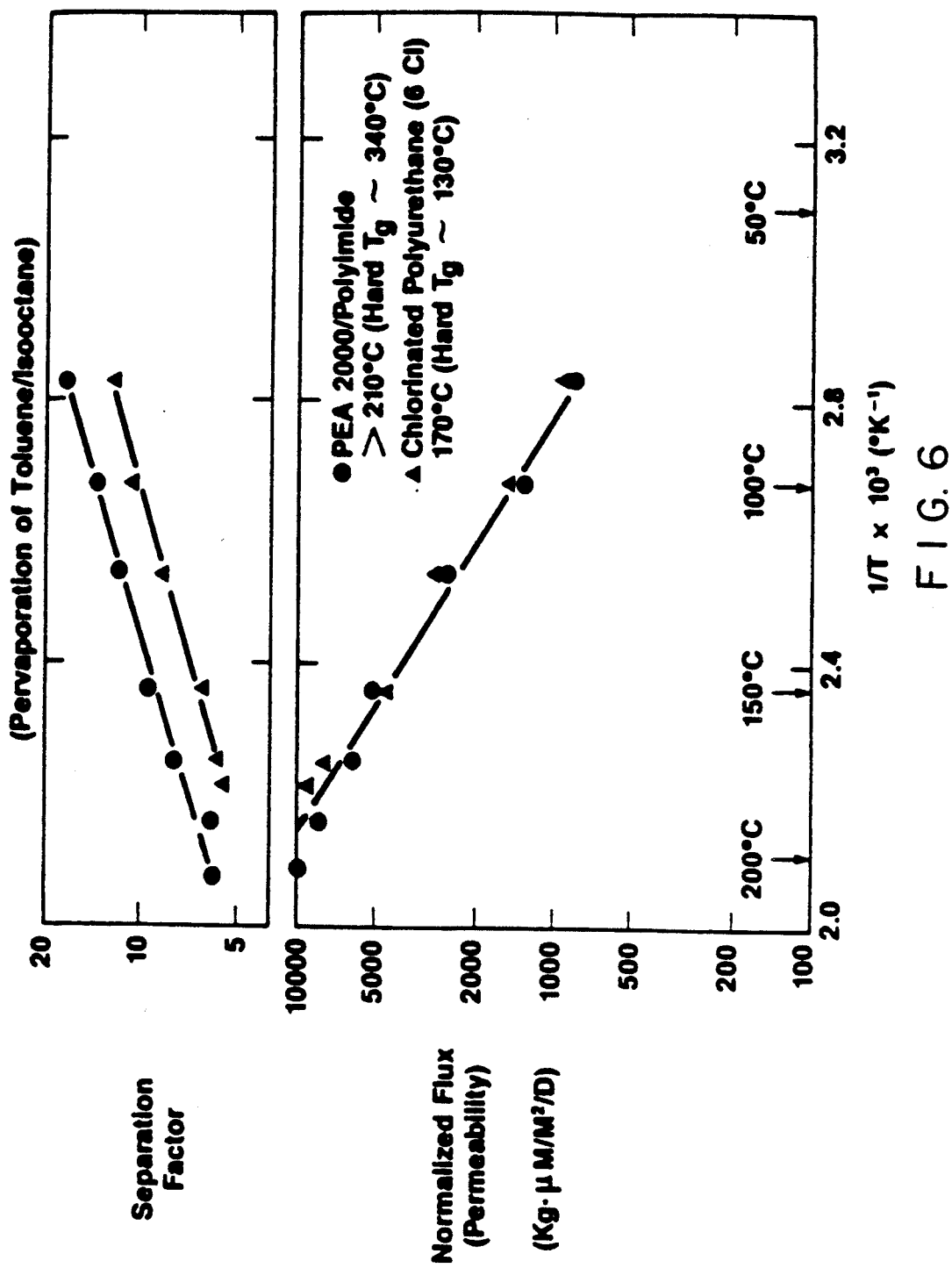
FIG. 6 shows the toluene/isooctane selectivity and permeability (flux) for a polyimide copolymer membrane of the present invention containing the soft segment of PEA 2000, and higher selectivity and thermal stability with this membrane than with the polyurethane membrane containing the hard segment with 6 chlorines.

The resulting membrane described in Example 1 was evaluated for aromatic/saturate separation with the feed mixture of 50 wt% toluene and 50 wt% isooctane in the pervaporation apparatus described above. FIG. 6 shows the toluene/isooctane selectivity and permeability for the polyimide copolymer membrane in comparison with those for a polyurethane membrane which contained the same soft segment of PEA 2000 and the highly chlorinated hard segment with 6 chlorines, as shown in FIG. 3. The highly chlorinated polyurethane membrane had the same selectivity and permeability as the polyurethane membrane without Cl, as shown in FIG. 3, containing the same soft segment; however, the former had a high thermal stability of about 170° C. whereas the latter had a stability of about 100° C. As shown in the figure, the polyimide copolymer membrane had about the same permeability as the highly chlorinated polyurethane membrane at a given temperature up to about 170° C. However, the polyimide copolymer membrane had higher selectivity than the chlorinated polyurethane membrane. This polyimide copolymer membrane was stable at least up to 210° C., which was the maximum temperature capability of the pervaporation apparatus. Thus, this membrane has exhibited the highest thermal stability among the membranes investigated. The high thermal stability of this membrane was presumably due to its polyimide hard segment having a high glass transition temperature (Tg) of about 340° C. as determined from differential scanning calorimetry (DSC). This Tg was much higher than that of the hard segment of the chlorinated polyurethane membrane, about 130° C. However, the soft segment Tg values for the polyimide copolymer and polyurethane membranes were about the same, about −25° C. Thus, these results have reinforced our finding that the hard segment provides thermal stability.

In addition to the thermal stability and selectivity advantages described above for the polyimide copolymer membrane vs. the polyurethane membrane, the former membrane had better solvent resistance than the latter. For example, the polyimide copolymer membrane was insoluble in DMF, whereas the polyurethane membrane was soluble in the solvent.

EXAMPLE 3

Synthesis of the Polyimide Copolymer Containing the Polyethylene Adipate Soft Segment with a Molecular Weight of 1000

The procedure was the same as that described in Example 1 except polyethylene adipate diol with a molecular weight of 1000 (PEA 1000) was used instead of PEA 2000. The resulting membrane had a thickness of about 45 microns.

EXAMPLE 4

Pervaporation Results for the Polyimide Copolymer Membrane Containing the Polyethylene Adipate Soft Segment with a Molecular Weight of 1000

Figure 7:
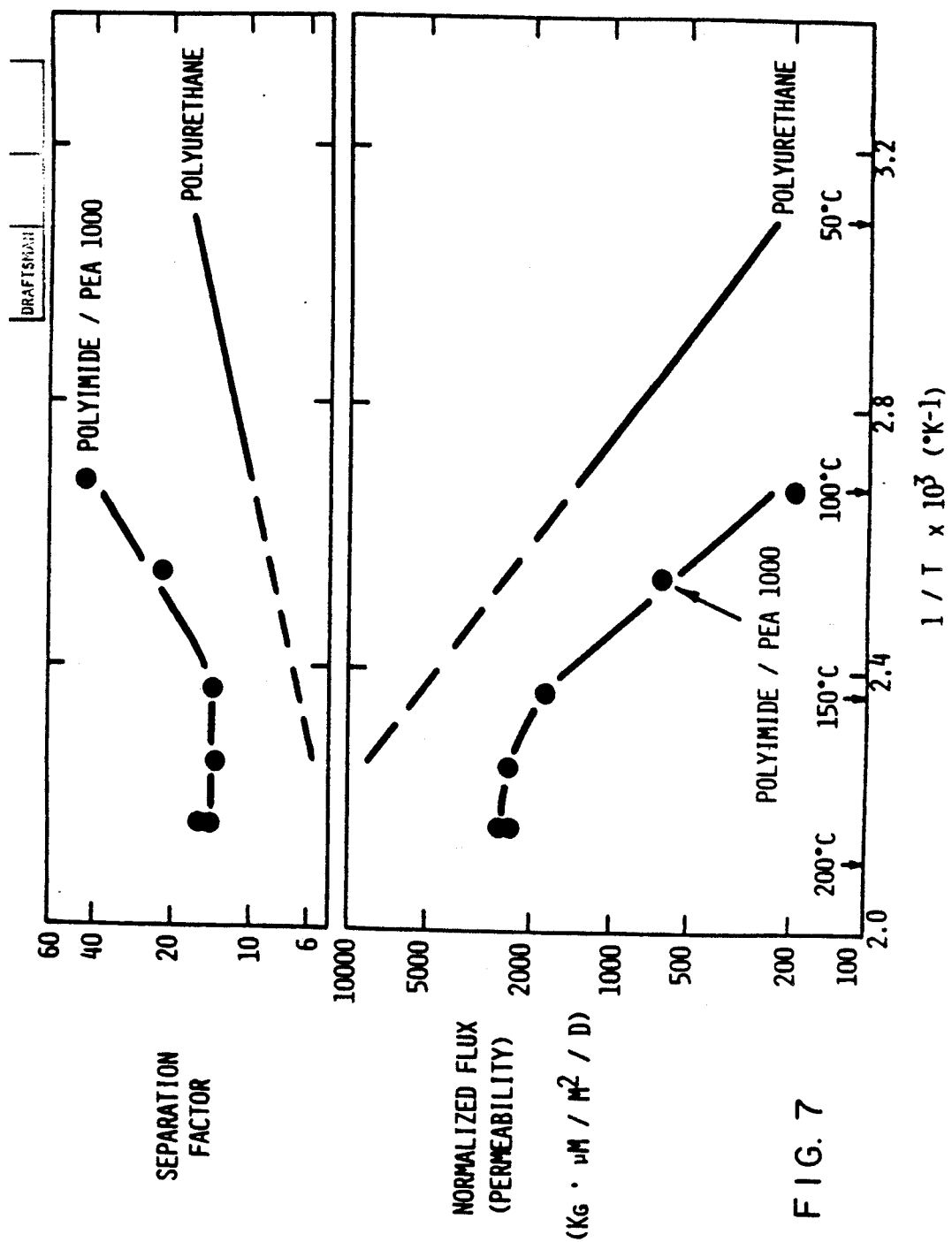
FIG. 7 shows the toluene/isooctane selectivity and permeability for another polyimide copolymer membrane of the present invention containing the soft segment of polyethylene adipate with a molecular weight of 1000 (PEA 1000).

The resulting membrane described in Example 3 was evaluated in a similar way as described in Example 2. FIG. 7 shows the toluene/isooctane selectivity and permeability for the polyimide copolymer membrane containing the soft segment of PEA 1000. The selectivity decreased from about 40 at 100° C. to 14 at 150° C., and it remained fairly constant from 150° C. to 190° C. On the other hand, the permeability increased significantly from about 200 Kg·$\mu$M/M$^2$/D at 100° C. to 1800 Kg·$\mu$M/M$^2$/D at 150° C., and it increased slightly to about 2500 Kg·$\mu$M/M$^2$/D at 190° C. The constant selectivity and the slight permeability increase from 150° C. to 190° C. were presumably due to the constant degree of swelling or solubility for this membrane reached at this temperature range. At the constant swelling or solubility, the solubility ratio between toluene and isooctane should be fairly constant, and their diffusivity ratio was also fairly constant because the diffusivities were primarily a function of solubility at a given temperature. These resulted in the constant selectivity. The constant selectivity behavior gives a reasonably good selectivity at high temperatures, and this is desirable for high-temperature separations. The slight permeability increase was due to the increase of the diffusivities with increasing temperature in the absence of the solubility increase with temperature.

As shown in FIG. 7, the polyimide copolymer with the PEA 1000 soft segment had higher toluene/ isooctane selectivity but lower permeability than the polyurethane without Cl, as shown in FIG. 3, containing the soft segment of PEA 2000. In comparison of this figure with FIG. 6, this polyimide copolymer also had higher selectivity but lower permeability than the polyimide copolymer with the soft segment of PEA 2000. The higher selectivity and lower permeability with the PEA 1000 soft segment were presumably due to narrower inter-segmental spacing, i.e., a tighter polymer matrix vs. the case with PEA 2000 soft segment.

EXAMPLE 5

Synthesis of the Polyimide Copolymer with the Soft Segment of Mixed Polyethylene Adipates The procedure was the same as that described in Example 1 except a mixture of polyethylene adipate diol with a molecular weight of 500 (PEA 500) and polyethylene adipate diol with a molecular weight of 2000 (PEA 2000) at a molar ratio of 0.7 to 0.3 was used instead of only PEA 2000. The resulting membrane had a thickness of about 38 microns.

EXAMPLE 6

Figure 8:
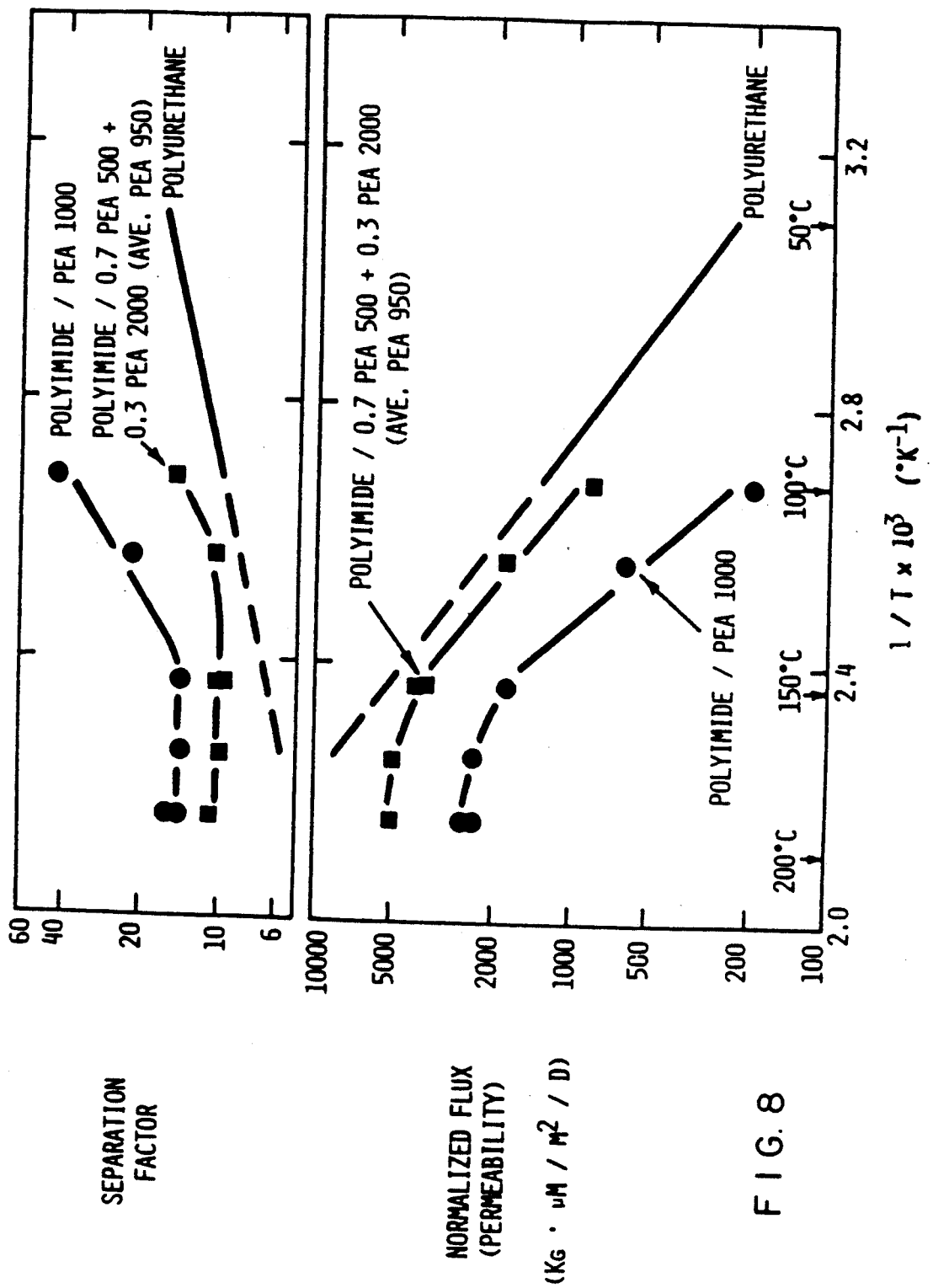
FIG. 8 shows that a polyimide copolymer with single polyadipate has higher selectivity but lower permeability than that with mixed polyadipates.

Pervaporation Results for the Polyimide Copolymer with the Soft Segment of Mixed Polyethylene Adipates The resulting membrane described in Example 5 was evaluated in a similar way as described in Example 2. FIG. 8 shows the toluene/isooctane selectivity and permeability for the polyimide copolymer with the soft segment containing a mixture of polyethylene adipate with a molecular weight of 500 (PEA 500) and polyethylene adipate with a molecular weight of 2000 (PEA 2000) at a molar ratio of 0.7 to 0.3. The soft segment had an average molecular weight of about 950. This molecular weight was very close to that for the soft segment of the polyimide copolymer containing the single polyethylene adipate, PEA 1000. In FIG. 8, the selectivity and permeability results for the polyimide copolymer with the PEA 1000 soft segment and the polyurethane without Cl as shown in FIG. 7 are reproduced for comparison. As shown in FIG. 8, with about the same soft-segment molecular weight of 1000, the polyimide copolymer with the soft segment containing the mixed PEA 500 and PEA 2000 had lower selectivity but higher permeability than that with the soft segment of the single PEA 1000. Presumably, this was due to the enhanced swelling (solubility) of the soft segment containing PEA 2000. In the similar behavior as the polyimide copolymer with the PEA 1000 soft segment discussed above, the polyimide copolymer with the soft segment of the mixed polyethylene adipates had a nearly constant value for the selectivity and a slight increase for the permeability with increasing temperature from 150° C. to 190° C. Also shown in FIG. 8, the polyimide copolymer with the mixed polyadipates had higher selectivity but lower permeability than the polyurethane.

EXAMPLE 7

Synthesis of the New Copolymer, With Polyethylene Succinate/PMDA/MOCA at a Mole Ratio of 1/2/1, Containing 29 wt% Polyimide Hard Segment and 71 wt% Polyethylene Succinate Soft Segment To 2.18 g (0.01 mole) of pulverized pyromellitic dianhydride (PMDA) heated (about 105° C.) under $N_2$ in a reactor was added 10 g (0.005) mole of polyethylene succinate diol with a molecular weight of about 2000 (PES) with stirring. The temperature was about 105° C., and the stirring continued for about 5 hours to complete the end-capping step. To the reactor content was added 41.3 g of DMF, and the temperature was dropped to about 80° C. with stirring for about 0.5 hour. To this reactor content was added 1.34 g (0.005 mole) MOCA in 10 g DMF solution dropwise. The solution was stirred at 80° C. for 2.5 hours. Then, a viscous solution resulted, which indicated the chain-extension reaction. The solution was then cooled to room temperature. The resulting solution containing the copolymer with the polyamic acid hard segment and the polyethylene succinate soft segment had suitable consistency for solution casting in the preparation of membranes.

The resulting solution was centrifuged for about 5 minutes. Following centrifugation, a membrane was knife-cast onto a glass plate with a knife gap setting of 13 mils. DMF was allowed to evaporate from the membrane in a nitrogen box in a hood at ambient conditions over a period of about 17 hours. The membrane was then dried in an oven at 90° C. for 2 hours. The membrane was removed from the glass plate by soaking it in a water bath. Then, the membrane was dried at 120° C. for about 39 hours. Finally, the membrane was heated to 300° C., maintained at this temperature for 1.5 hours and then cooled to room temperature in the curing step. The resulting membrane synthesized from PES/PMDA/MOCA at a molar ratio of 1/2/1 contained 29 wt% polyimide hard segment and 71 wt% polyethylene succinate soft segment, and it had a thickness of about 16 microns.

EXAMPLE 8

Synthesis of the New Copolymer, With Polyethylene Succinate/PMDA/MOCA at a Molar Ratio of 1/3/2, Containing 40 wt% Polyimide Hard Segment and 60 wt% Polyethylene Succinate Soft Segment To 1.05 g (0.0048 mole) of pulverized pyromellitic dianhydride (PMDA) heated (about 110° C.) under $N_2$ in a reactor was added 4 g (0.0024 mole) of polyethylene succinate diol with a molecular weight of 1667 (PES) with stirring. The temperature was about 110° C., and the stirring continued for about 4 hours to complete the end-capping step. To the reactor content was added 3 g of DMF, and the stirring was continued for 1 hour at 110° C. An additional 37 g of DMF was added, and the temperature was dropped to about 80° C. with stirring for about 0.5 hour. To this reactor content was added 1.29 g (0.0048 mole) MOCA in 10 g DMF solution at once. The stirring was continued for another hour. Then, 0.52 g (0.0024 mole) of PMDA and 5.9 g of DMF were added, the stirring was continued for another hour at 80° C. Then, a viscous solution resulted, which indicated the chain-extension reaction. The solution was then cooled to room temperature. The resulting solution containing the copolymer with the polyamic acid hard segment and the polyethylene succinate soft segment had suitable consistency for solution casting in the preparation of membranes.

The resulting solution was centrifuged for about 5 minutes. Following centrifugation, a membrane was knife-cast onto a glass plate with a knife gap setting of 12 mils. DMF was allowed to evaporate from the membrane in a nitrogen box in a hood at ambient conditions over a period of about 17 hours. The membrane was then dried in an oven at 90° C. for 2 hours. The membrane was removed from the glass plate by soaking it in a water bath. Then, the membrane was dried at 120° C. overnight. Finally, the membrane was heated to 300° C., maintained at this temperature for 1.5 hours and then cooled to room temperature. The resulting membrane synthesized from PES/PMDA/MOCA at a molar ratio of 1/3/2 contained 40 wt% polyimide hard segment and 60 wt% polyethylene succinate soft segment, and it had a thickness of about 37 microns.

EXAMPLE 9

Pervaporation Results for Polyimide/Polysuccinate Copolymer Membranes

The resulting membranes described in Examples 7 and 8 were evaluated for aromatics/saturates separation with the feed mixture of 10 wt% toluene, 40 wt% p-xylene, 20 wt% isooctane and 30 wt% n-octane in the pervaporation apparatus described above.

As shown in Table 2, for pervaporation at 150° C., the polyimide/polysuccinate copolymer membrane containing 29 wt% of the polyimide hard segment and 71 wt% of the soft segment of PES (which was synthesized from PES, PMDA, and MOCA at a molar ratio of 1/2/1) had an overall aromatics/saturates separation factor of 9 and a permeability (normalized flux) of about 600 Kg-$\mu$M/M$^2$/day. This membrane had a much higher selectivity than the polyimide/polyadipate copolymer containing the same hard segment and the soft segment of polyethylene adipate (PEA) with a molecular weight of 2000 (which was synthesized from PEA 2000, pyromellitic dianhydride and MOCA at a molar ratio of 1/2/1 as described in Example 1). The former membrane had a lower permeability than the latter. This polyimide/polysuccinate copolymer membrane had the same selectivity but much higher permeability than the second polyimide/polyadipate copolymer membrane, shown in this table, containing the soft segment of PEA 500 (which was synthesized from PEA 500, pyromellitic dianhydride and MOCA at a molar ratio of 1/3/2). The polyimide/polyadipate copolymer had a permeability of about 60 Kg·μM/M²/D.

TABLE 2

POLYIMIDE/POLYSUCCINATE GIVES IMPROVED SELECTIVITY/FLUX

| Membrane | Aromatics/Saturates Separation Factor | Flux (Permeability) (Kg · μM/M²/D) |
|---|---|---|
| Polyimide/Polyadipate (MW 2000) | 5 | 3000 |
| Polyimide/Polyadipate (MW 500) | 9 | 60 |
| Polyimide/Polysuccinate (29/71) | 9 | 600 |
| Polyimide/Polysuccinate (40/60) | 10.7 | 200 |

The second polyimide/polysuccinate copolymer membrane, shown in this table, containing 40 wt% of the polyimide hard segment and 60 wt% of the PES soft segment (which was synthesized from PES, pyromellitic dianhydride and MOCA at a molar ratio of 1/3/2) had a separation factor of 10.7 and a permeability of about 200 Kg·μM/M²/D. This membrane had a higher selectivity but a lower permeability than the first polyimide/polysuccinate membrane with 29 wt% of the hard segment. Thus, increasing hard segment fraction enhances selectivity but reduces permeability owing to a lower degree of swelling for the soft segment in the presence of penetrant molecules. This second polyimide/polysuccinate copolymer membrane had higher selectivity and permeability than the polyimide/polyadipate copolymer membrane with the soft segment of PEA 500.

Figure 9:
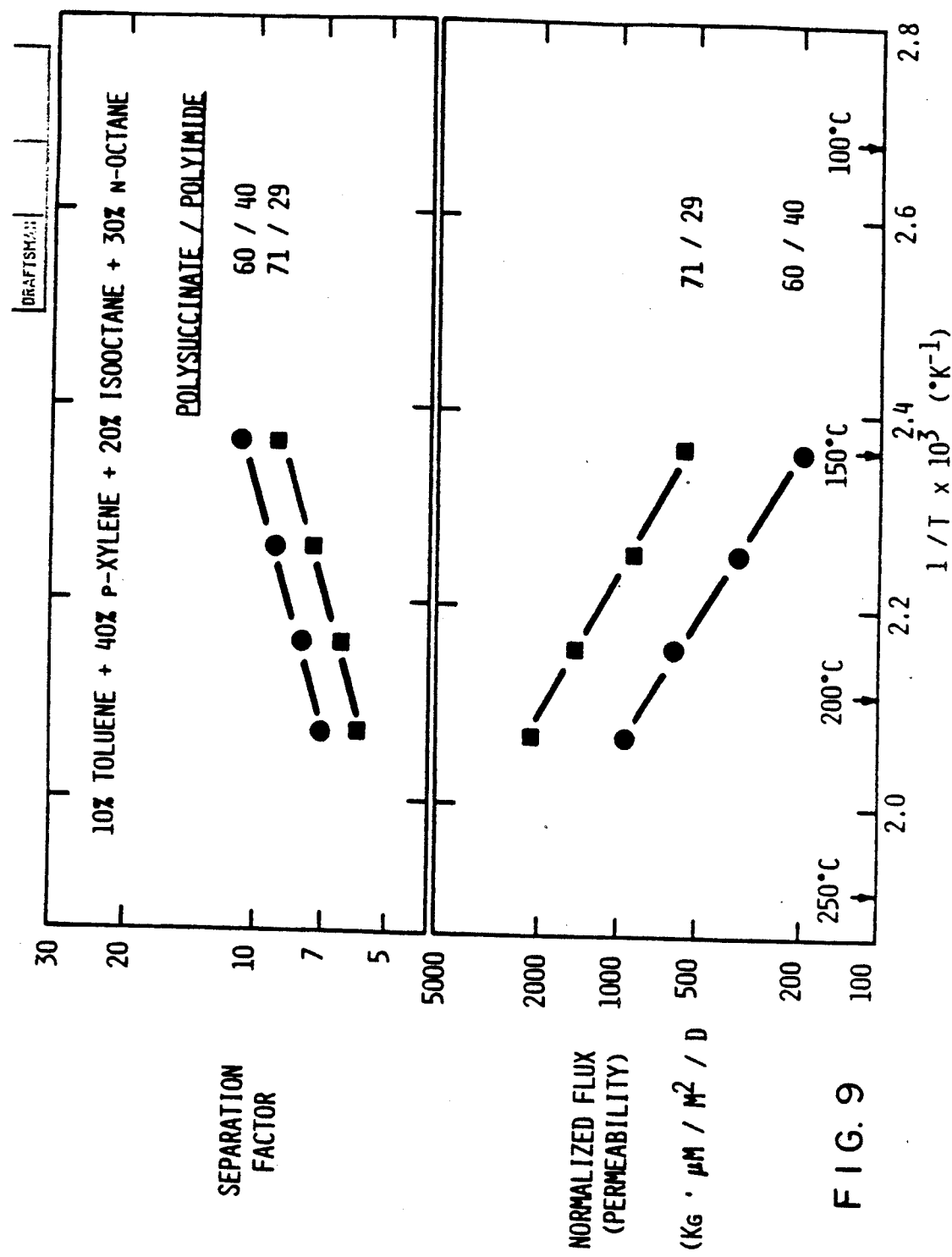
FIG. 9 shows that increasing polyimide hard segment fraction improves overall aromatics/saturates selectivity but decreases permeability (flux).
Figure 10:
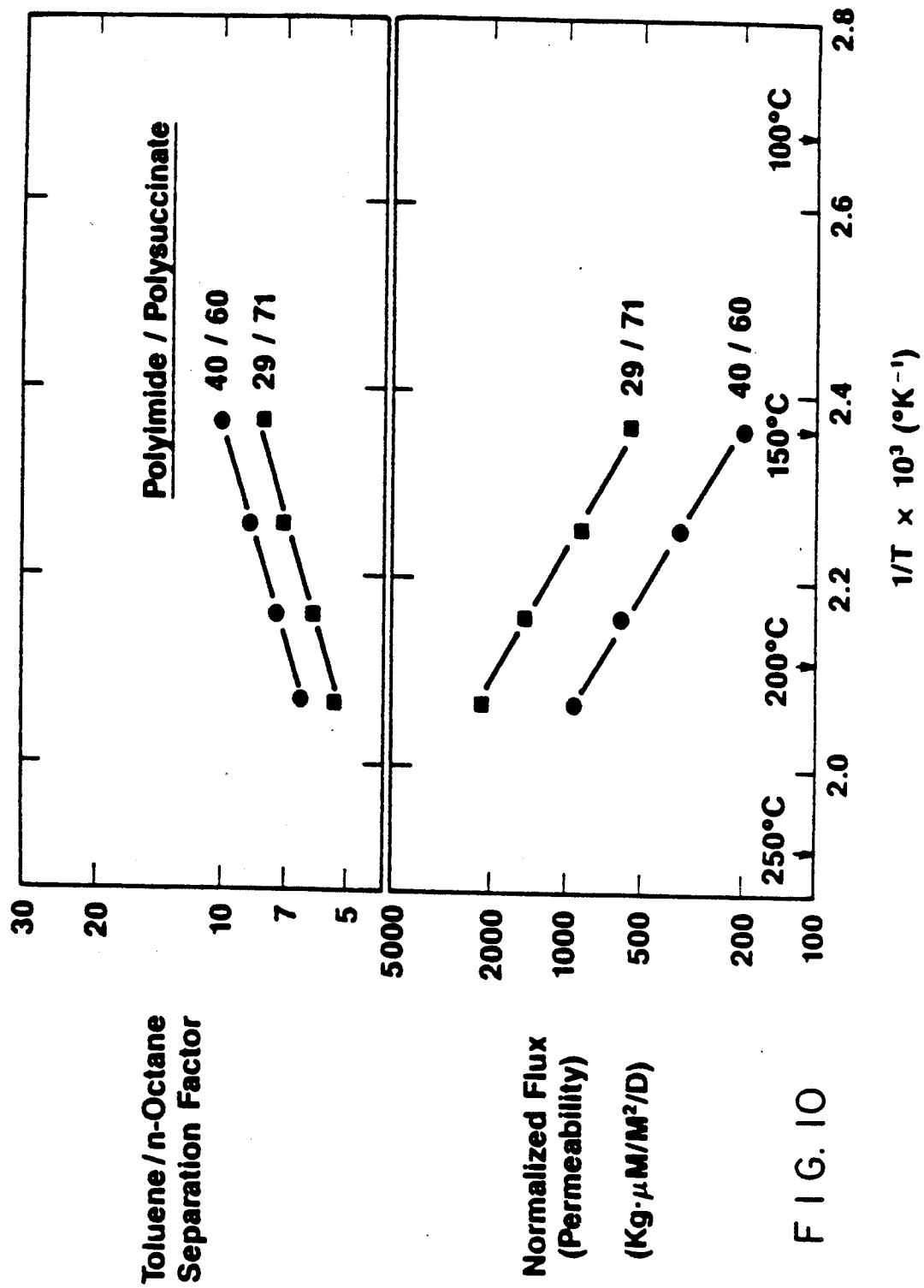
FIG. 10 shows that increasing polyimide hard segment fraction improves toluene/n-octane selectivity but reduces permeability (flux).
Figure 11:
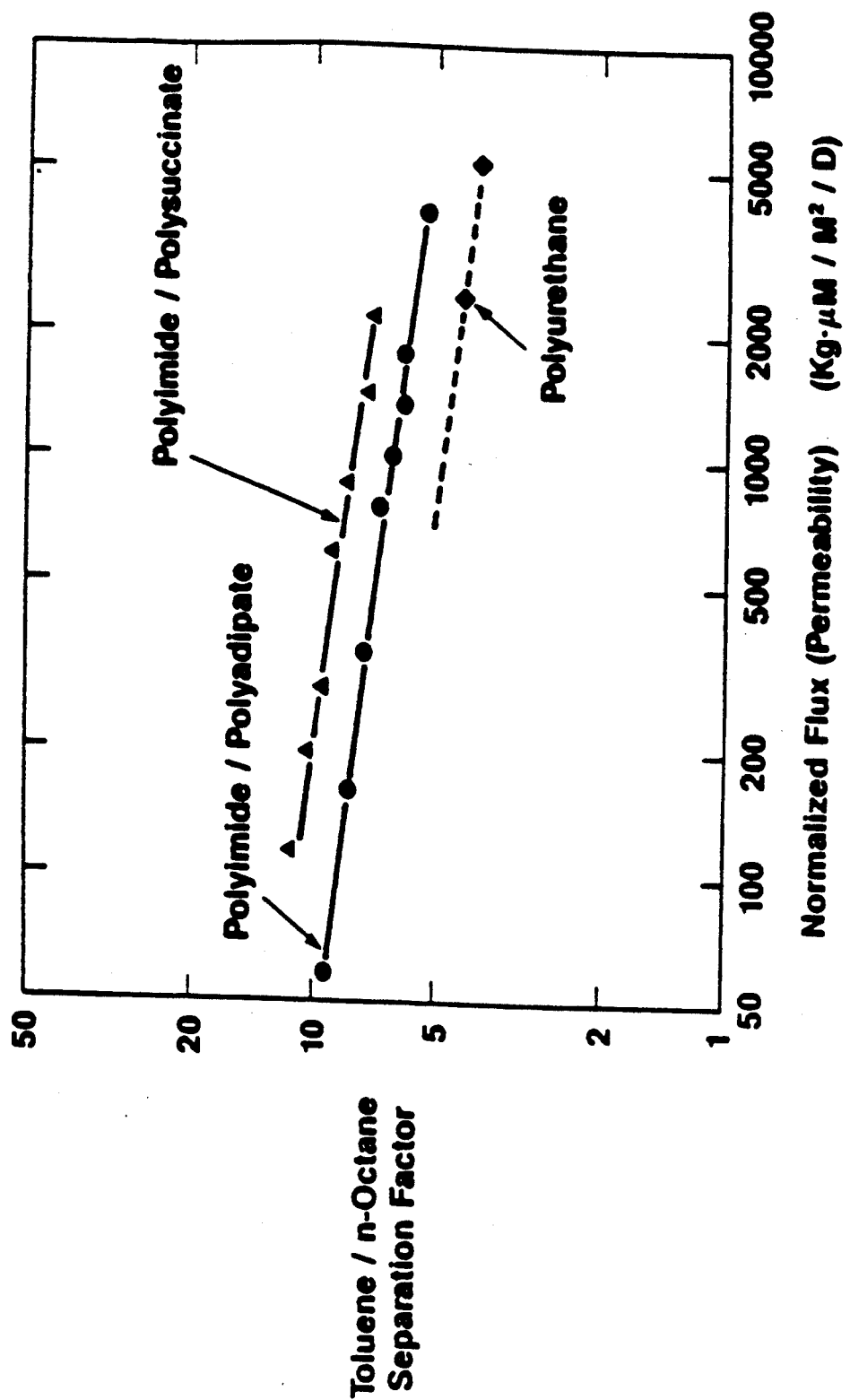
FIG. 11 shows that the new membranes of the present invention, polyimide/polysuccinate and polyimide/polyadipate copolymer membranes, give improved selectivity and flux vs. the membranes investigated.

FIG. 9 shows the overall aromatics/ saturates selectivity and permeability results whereas FIG. 10 shows the toluene/n-octane selectivity and permeability results for the polyimide/polysuccinate copolymer membranes in the pervaporation of the model feed as a function of temperature from 150° C. to 210° C. For the temperature range investigated, increasing hard segment fraction improves selectivity but decreases permeability. As shown in these figures, these membranes were run up to 210° C. and were stable at this temperature, which was the maximum temperature capability of the pervaporation apparatus. Thus, these membranes have exhibited the highest thermal stability among the membranes investigated. As shown in FIG. 11, these membranes show higher selectivity at a given permeability than polyimide/polyadipate and polyurethane membranes.

EXAMPLE 10

Thin-Film-Composite Membrane of the Polyimide Copolymer Containing the Soft Segment of Polyethylene Adipate with a Molecular Weight of 2000

Figure 12:
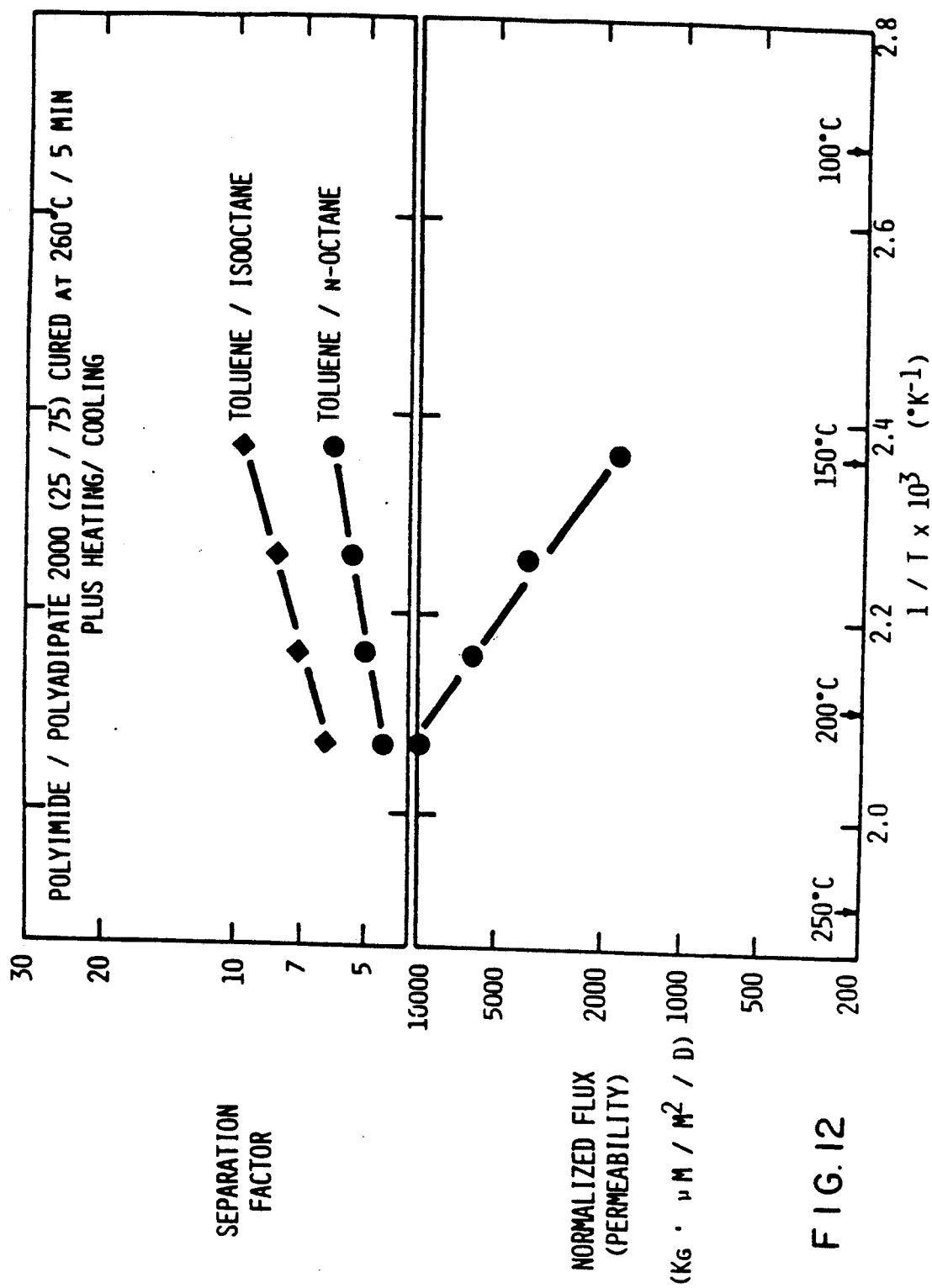
FIG. 12 shows the toluene/isooctane and toluene/n-octane selectivities and permeability for a polyimide copolymer of the present invention, containing the soft segment of polyethylene adipate with a molecular weight of 2000 (PEA 2000), cured at 260° C. for 5 minutes.

A thin-film-composite membrane of the polyimide copolymer containing the soft segment of polyethylene adipate with a molecular weight of 2000 (PEA 2000) was synthesized via the same procedure as described in Example 1 except (1) the solution was cast onto a microporous teflon support with about 50 micron thickness, 0.2 micron pores and 80% porosity instead of casting onto a glass plate and there was no need to soak the thin-film-composite membrane into water as in the case of Example 1 to release the membrane from the glass plate, and (2) the membrane was cured by heating from room temperature to 260° C., maintaining it at this temperature for 5 minutes and then cooling it to room temperature. The resulting membrane had a thickness of about 20 microns excluding the microporous support, and it had a polyimide/polyadipate weight ratio of 25/75. The membrane was evaluated for aromatics/saturates separation with the feed mixture of 10 wt% toluene, 40 wt% p-xylene, 20 wt% isooctane and 30 wt% n-octane in the pervaporation apparatus described above. FIG. 12 shows toluene/isooctane and toluene/n-octane separation factors and flux from 150° C. to 210° C.

EXAMPLE 11

Thin-Film-Composite Membrane of the Polyimide Copolymer Containing the Soft Segment of Polyethylene Adipate with a Molecular Weight of 3000

Figure 13:
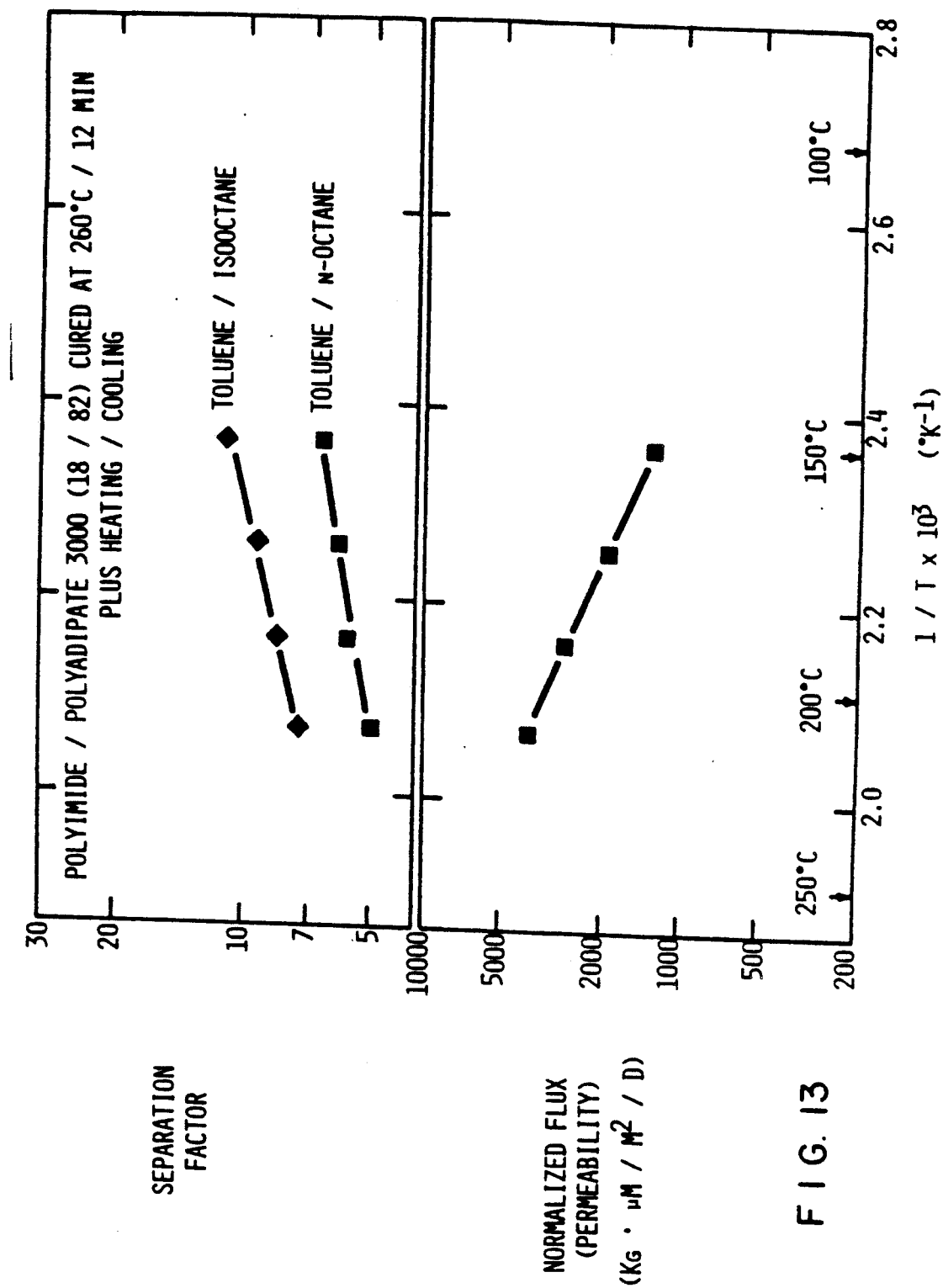
FIG. 13 shows the toluene/isooctane and toluene/n-octane selectivities and permeability for a polyimide copolymer of the present invention, containing the soft segment of polyethylene adipate with a molecular weight of 3000 (PEA 3000), cured at 260° C. for 12 minutes.

A thin-film-composite membrane of the polyimide copolymer containing the soft segment of polyethylene adipate with a molecular weight of 3000 (PEA 3000) was synthesized in the same way as described in Example 10 except PEA 3000 was used instead of PEA 2000 and the membrane was cured at 260° C. for 12 minutes instead of 5 minutes. The resulting membrane had a thickness of about 8 micron excluding the microporous support, and it had a polyimide/polyadipate weight ratio of 18/82. The membrane was evaluated for aromatics/saturates separation in the same way as described in Example 10. FIG. 13 shows toluene/isooctane and toluene/n-octane separation factors and flux from 150° C. to 210° C.

EXAMPLE 12

Effect of Membrane Thickness on Selectivity and Flux

A thin-film-composite membrane of the polyimide copolymer containing the soft segment of polyethylene adipate with a molecular weight of 2000 (PEA 2000) was synthesized in the same way as described in Example 10 except (1) the end-capping step was carried out at about 140° C. for about 1 hour and (2) the membrane had a thickness of about 7 microns excluding the microporous support. The resulting membrane had a polyimide/polyadipate weight ratio of 25/75.

Figure 14:
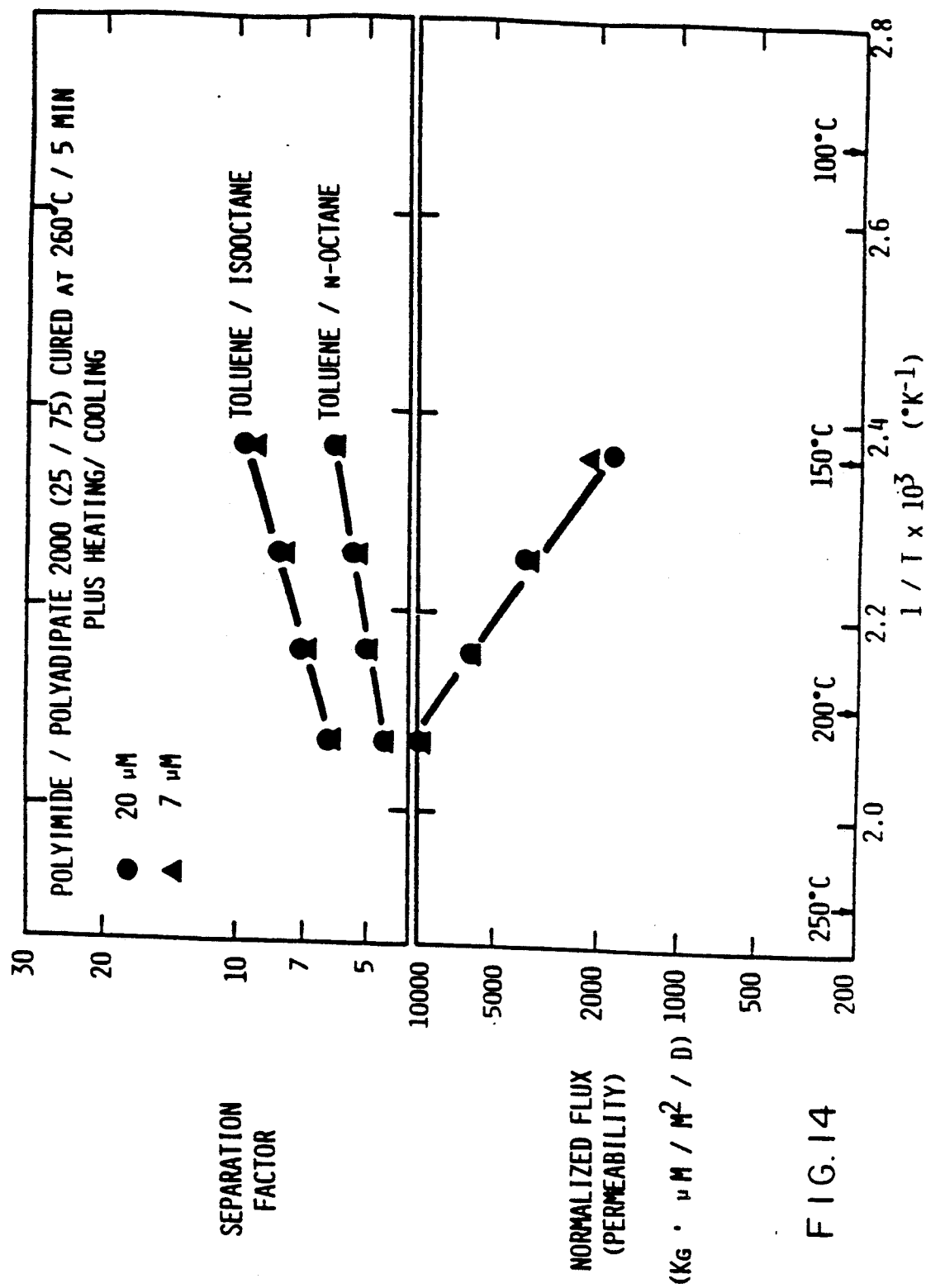
FIG. 14 shows that a thinner polyimide copolymer membrane has maintained the selectivity and permeability of a thicker one.
Figure 15:
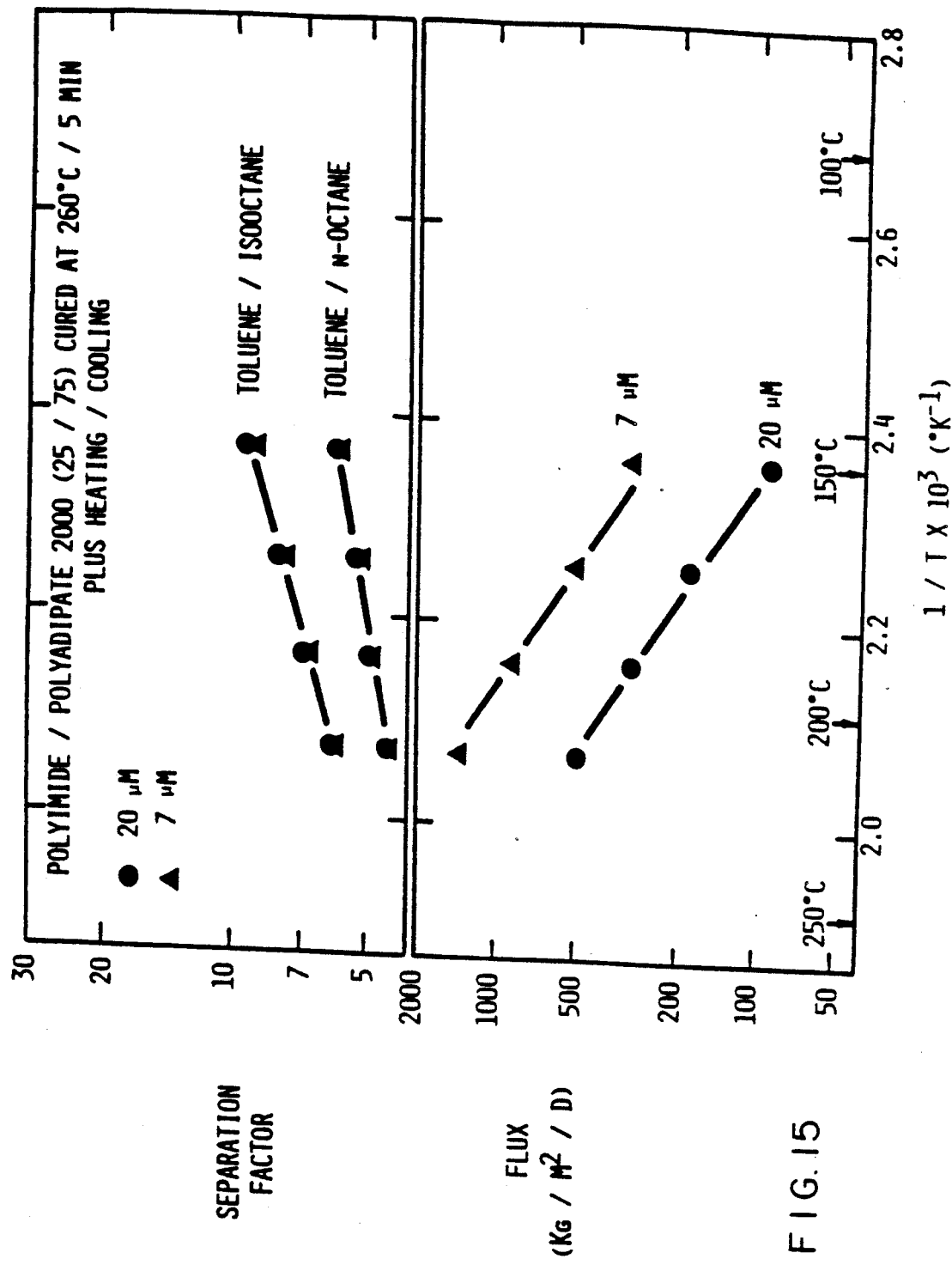
FIG. 15 shows that a thinner polyimide copolymer membrane has increased flux and maintained selectivity vs. a thicker one.

We evaluated the membrane of 7 microns in the same way as described in Example 10 for the membrane of 20 microns in pervaporation of the feed of 10 wt% toluene, 40 wt% p-xylene, 20 wt% isooctane and 30 wt% n-octane. FIG. 14 shows toluene/isooctane and toluene/n-octane separation factors and permeability from 150° C. to 210° C. The thinner membrane maintained the selectivity and permeability as the thicker membrane. The permeability result indicated that the flux for the polyimide copolymer membranes is proportional to the reciprocal of membrane thickness as predicted from the Fick law. FIG. 15 shows that the 7 micron membrane had much higher flux (about 3 times) than the 20 micron membrane.

EXAMPLE 13

Effect of Soft Segment Molecular Weight on Selectivity and Flux

Figure 16:
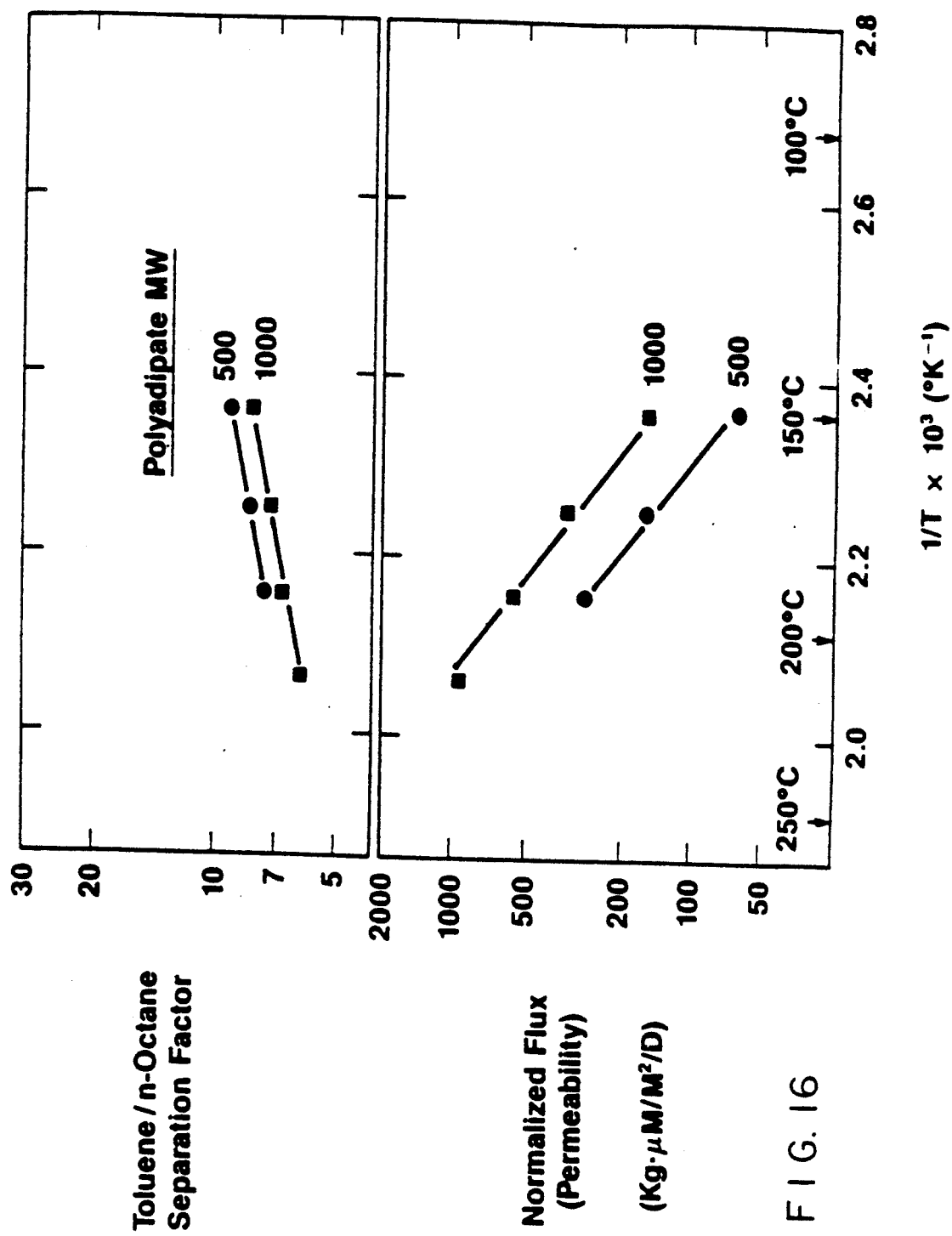
FIG. 16 shows that decreasing soft segment molecular weight increases selectivity but decreases permeability (flux).

Two polyimide copolymer membranes, (1) polyethylene adipate with a molecular weight of 500 (PEA 500) as the soft segment and (2) polyethylene adipate with a molecular weight of 1000 (PEA 1000) as the soft segment, were synthesized via the same procedure as described in Example 8 except PEA 500 and PEA 1000 were used instead of polyethylene succinate and they were thin-film-composite membranes. That is, these polyimide copolymer membranes had the soft segment/PMDA/MOCA at a molar ratio of 1/3/2. The first membrane had a thickness of about 35 microns and the second had about 1% microns (excluding the support). These membranes were evaluated for aromatics/saturates separation with the feed mixture of 10 wt% toluene, 40 wt% p-xylene, 20 wt% isooctane and 30 wt% n-octane in the pervaporation apparatus described above. FIG. 16 shows that decreasing soft segment molecular weight increases selectivity but decreases flux. As shown in this figure, the polyimide/polyadipate copolymer membrane containing the soft segment of PEA 500 had higher toluene/n-octane selectivity but lower flux than that with a soft segment of PEA 1000.

EXAMPLE 14

Figure 17:
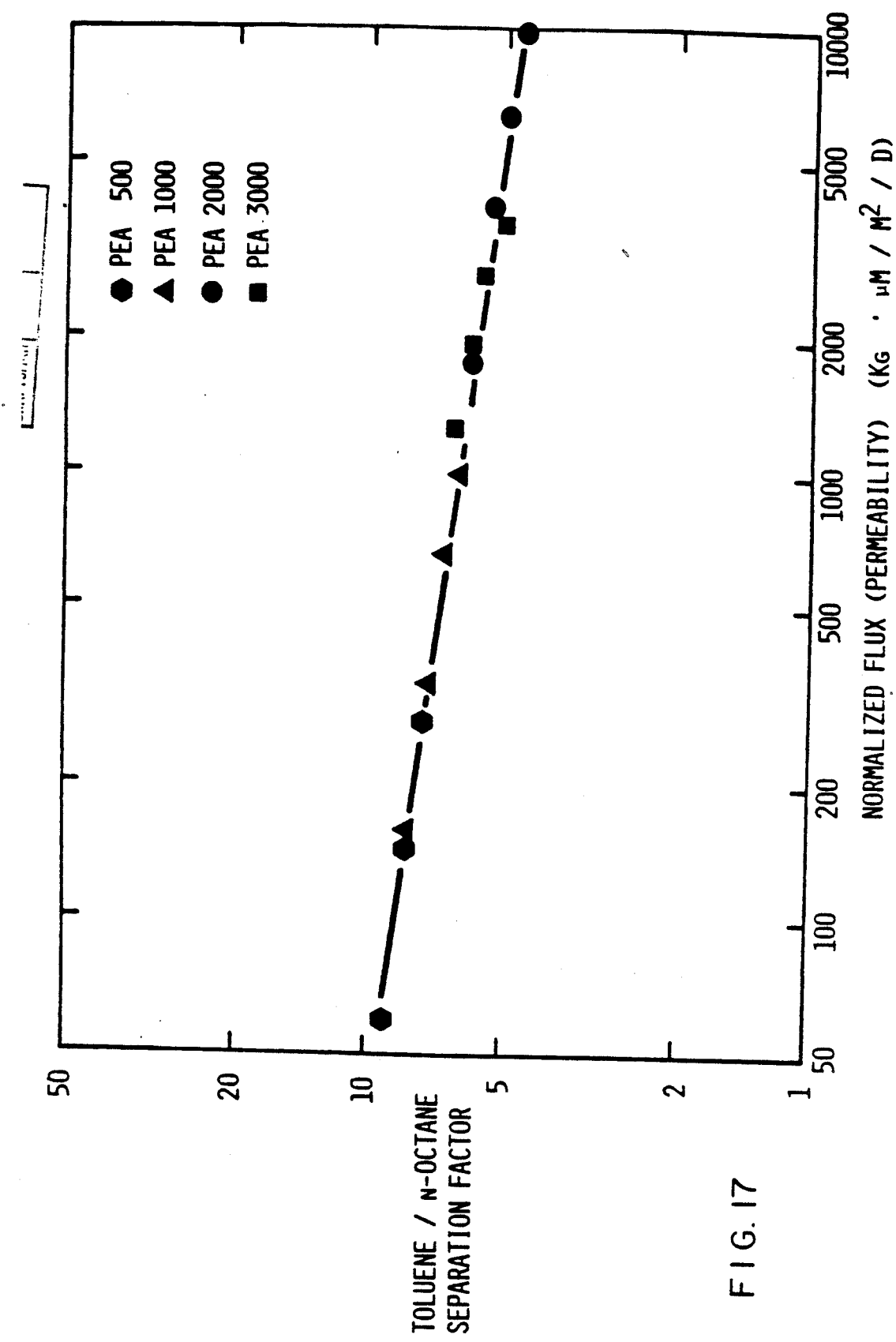
FIG. 17 shows that selectivity correlates with permeability for polyimide copolymers with various polyadipate molecular weights.

Selectivity-Permeability Relationship for Polyimide Copolymers with Various Polyadipate Molecular Weights We synthesized a family of polyimide copolymer membranes with the various molecular weights of polyethylene adipate soft segments, PEA 500, PEA 1000, PEA 2000, and PEA 3000 as described in Examples 10, 11 and 13. The toluene/n-octane selectivity and permeability results shown in FIGS. 12, 13, and 16 are replotted in a log-log scale in FIG. 17. As shown in this figure, selectivity correlates with permeability for the polyimide copolymer membranes with various polyadipate molecular weights. The permeability values cover a wide range from 60 to 10000 kg·μM/M²/D, i.e., over more than 2 orders of magnitude.

EXAMPLE 15

Selectivity-Permeability Relationship or Polyimide/Polyadipate Copolymers Cured at Different Conditions -- Effect of Curing on Selectivity and Flux A thin-film-composite membrane of the polyimide copolymer containing the soft segment of polyethylene adipate with a molecular weight of 2000 (PEA 2000) was synthesized in the same way as described in Example 10 except it was cured at 300° C. for 1.5 hours instead of 260° C. for 5 minutes. The resulting membrane had a thickness of about 28 microns excluding the microporous support, and it had a polyimide/polyadipate weight ratio of 25/75. The membrane was evaluated for aromatics/saturates separation in the same way as described in Example 10.

Figure 18:
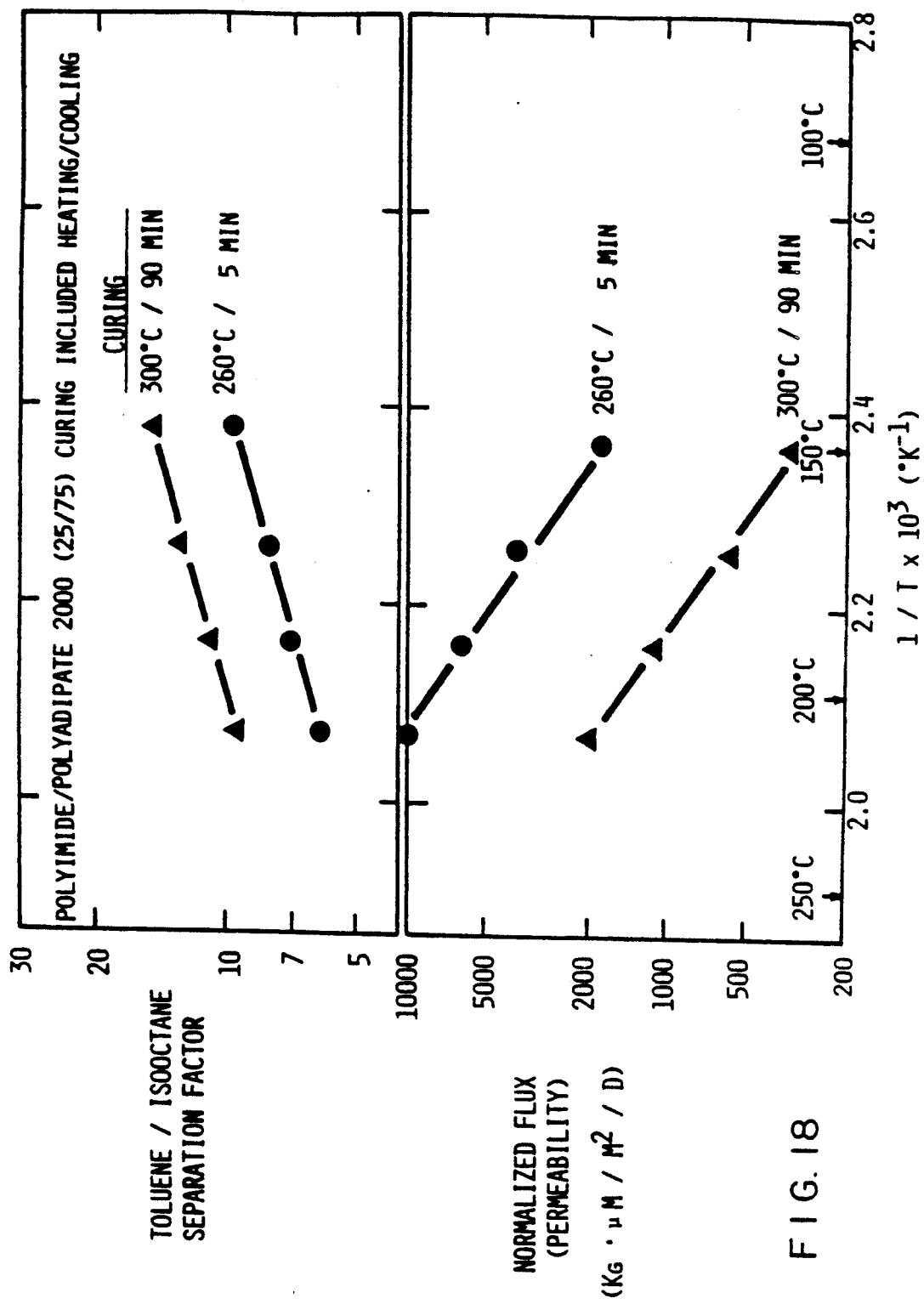
FIG. 18 shows that increasing curing severity improves toluene/isooctane selectivity but reduces permeability (flux).
Figure 19:
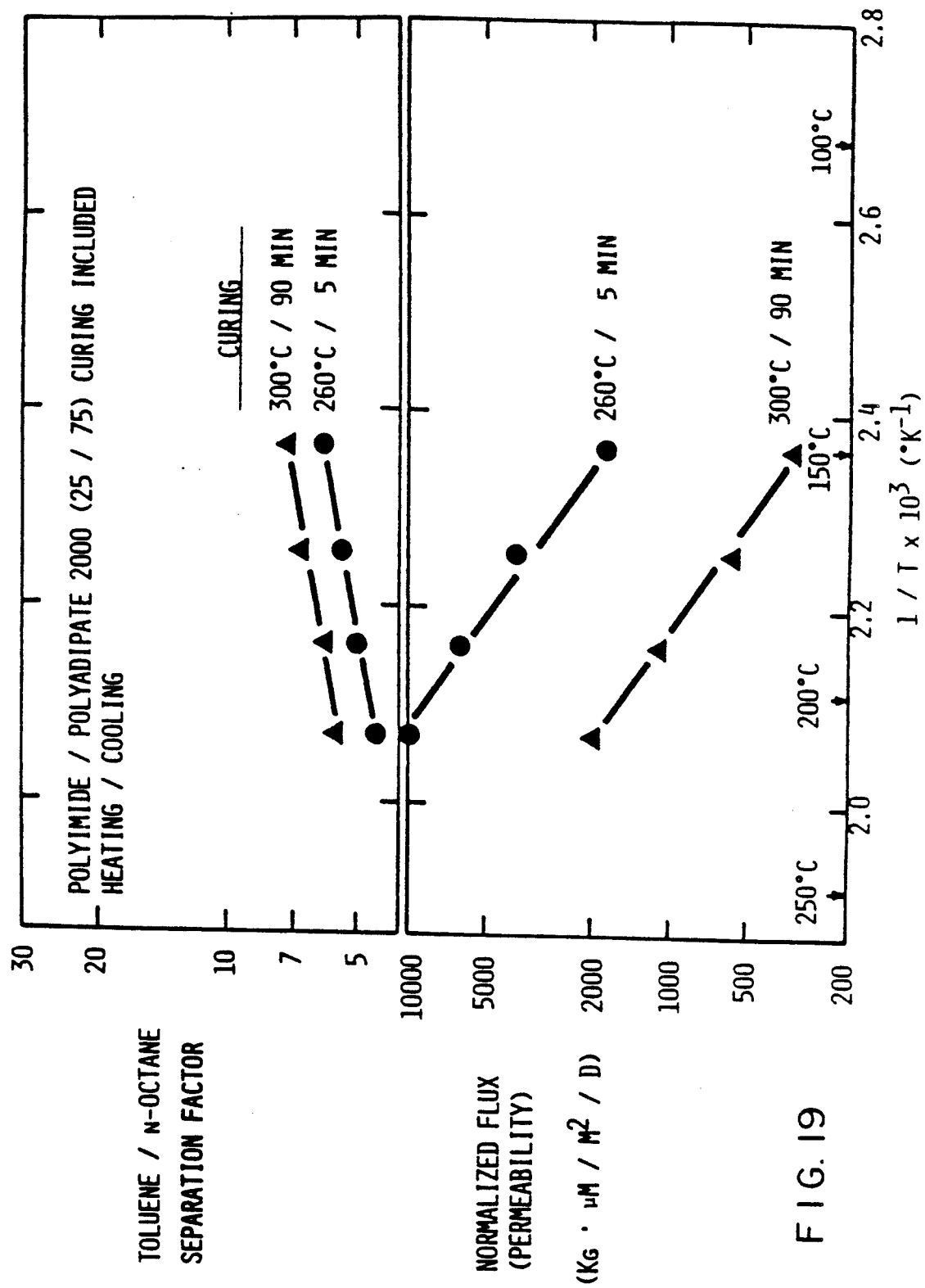
FIG. 19 shows that increasing curing severity improves toluene/n-octane selectivity but reduces permeability (flux).

FIG. 18 shows that increasing curing severity improves selectivity but reduces flux. In this figure, the toluene/isooctane selectivity and flux results for the polyimide/polyadipate copolymer membrane cured at 300° C. for 1.5 hours are compared with those for the membrane of the same composition but cured at 260° C. for 5 minutes, which are shown in FIG. 12 (Example 10). The former membrane with more severe curing had higher selectivity but lower flux than the latter with less curing. FIG. 19 shows the toluene/n-octane separation factors and flux results of these two membranes. Again, the membrane with more severe curing had higher selectivity but lower flux than that with less curing.

Figure 20:
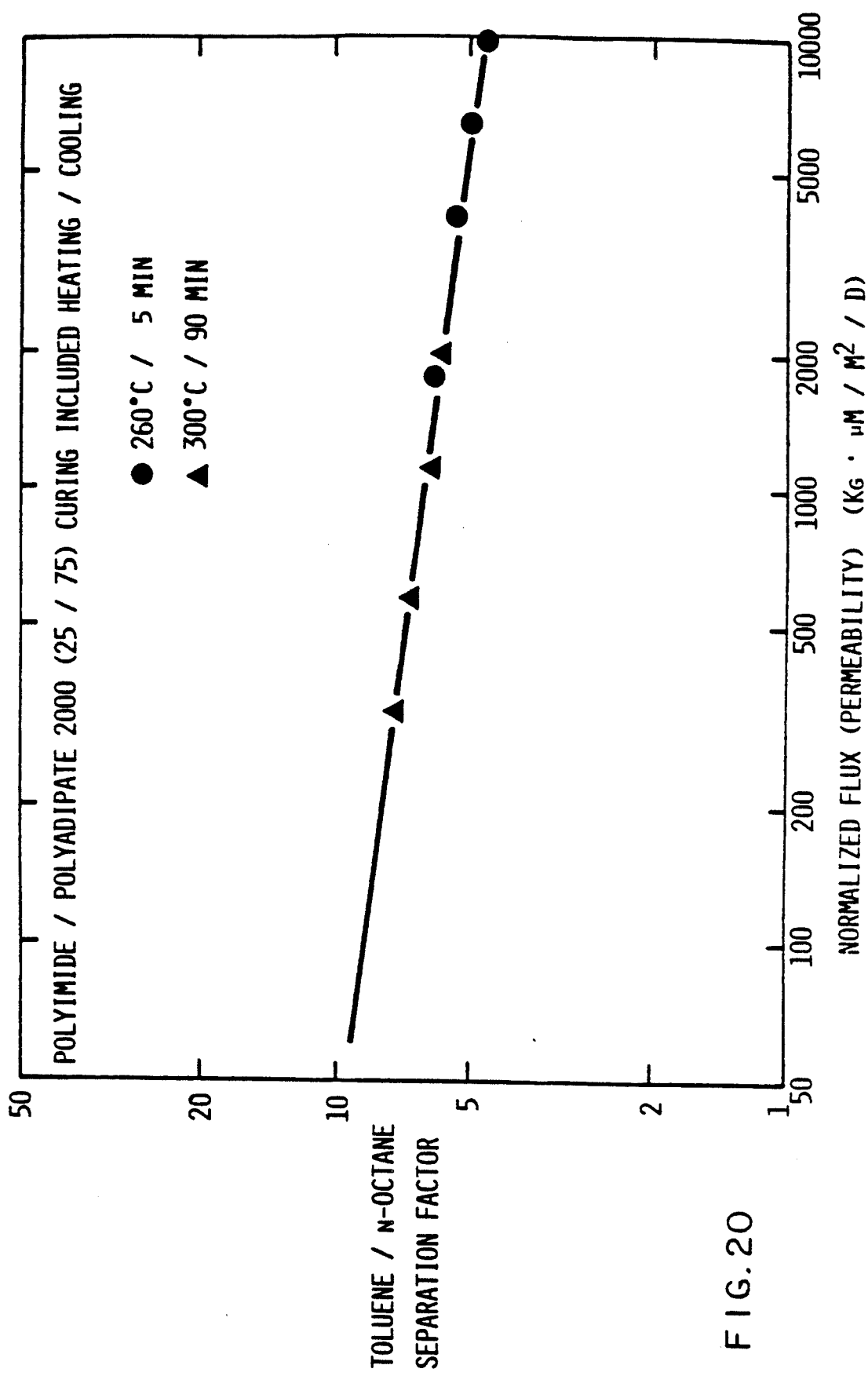
FIG. 20 shows that selectivity correlates with permeability for polyimide copolymers cured at different conditions.

We have replotted the selectivity and flux (permeability) results in FIG. 19 for these two membranes in FIG. 20 in the log-log plot described above. As shown in FIG. 20, selectivity correlates with permeability for the polyimide/polyadipate copolymer membranes of the same composition, i.e., the same polyadipate molecular weight, but cured at different conditions. The selectivity/permeability relationship agrees very well with that shown in FIG. 17 for the polyimide copolymer membranes with various polyadipate molecular weights, which is represented by the solid line in FIG. 20. As discussed above, FIG. 17 also includes the results for the polyimide copolymer membrane of polyadipate MW 3000 cured at 260° C. for 12 minutes, which is different from the curing conditions used for the two membranes with polyadipate MW 2000. Therefore, selectivity correlates with permeability for polyimide/polyadipate copolymer membranes with various polyadipate molecular weights and different curing conditions.

EXAMPLE 16

Effect of Curing on Selectivity and Flux

Figure 21:
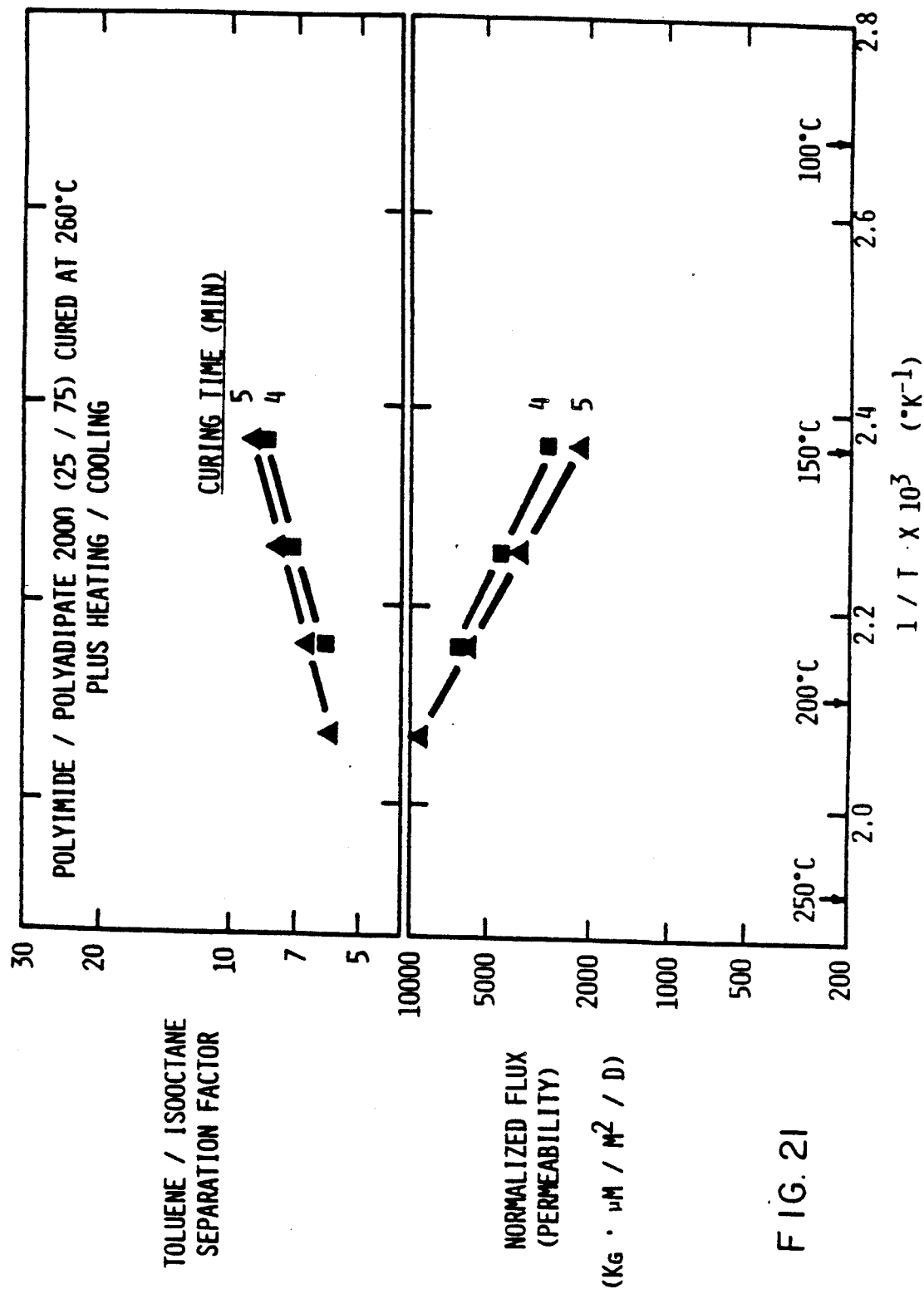
FIG. 21 shows the toluene/isooctane selectivities and permeabilities (fluxes) for the polyimide copolymer membranes, containing the soft segment of PEA 2000, cured at 260° C. for 4 and 5 minutes.
Figure 22:
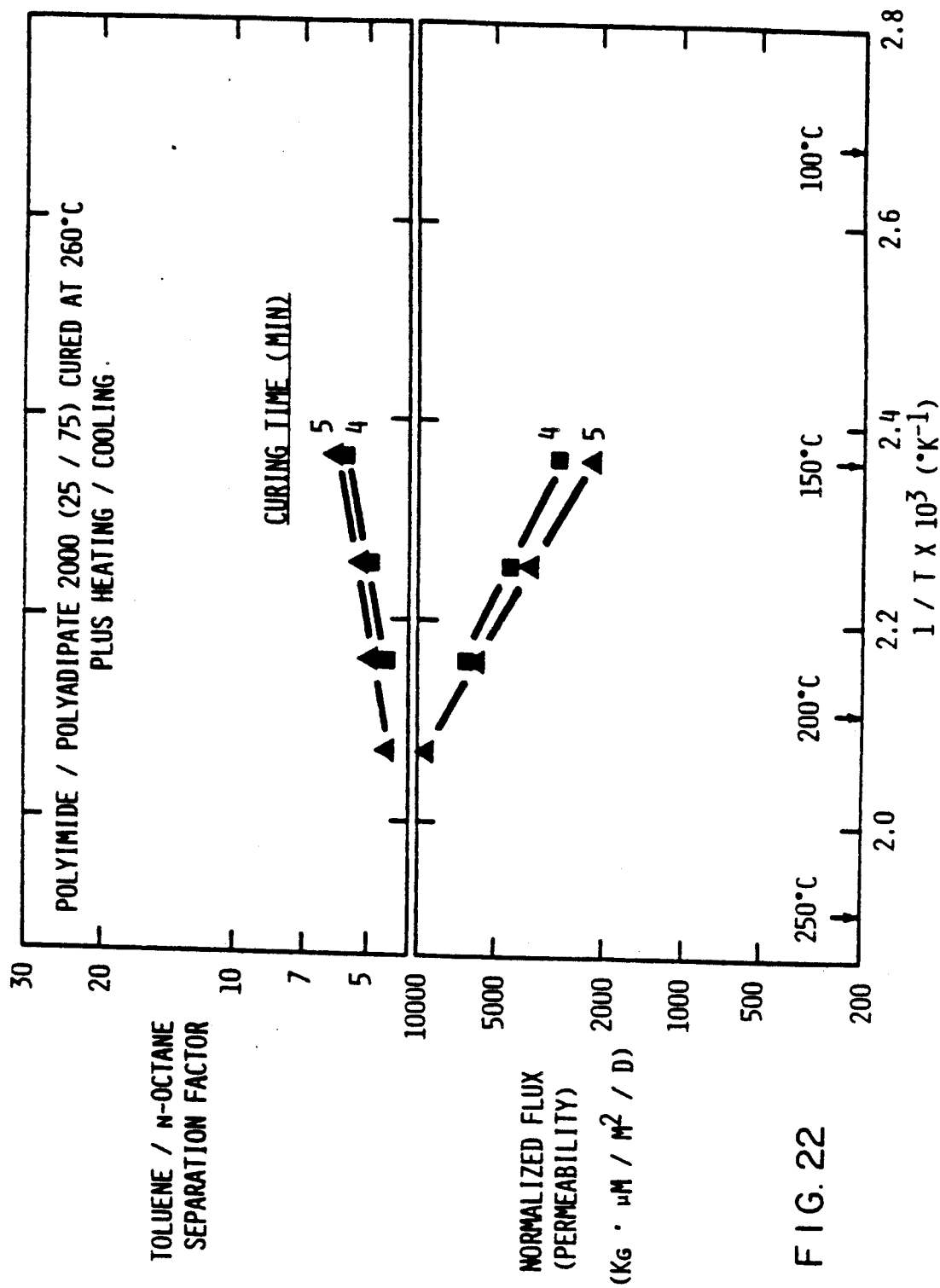
FIG. 22 shows the toluene/n-octane selectivities and permeabilities (fluxes) for the polyimide copolymer membranes, containing the soft segment of PEA 2000, cured at 260° C. for 4 and 5 minutes.

A thin-film-composite membrane of the polyimide copolymer containing the soft segment of polyethylene adipate with a molecular weight of 2000 (PEA 2000) was synthesized in the same way as described in Example 12 except the membrane was cured at 260° C. for 4 minutes instead of 5 minutes. The resulting membrane had a thickness of about 7 microns excluding the microporous support, and it had a polyimide/polyadipate weight ratio of 25/75. This membrane was evaluated for aromatics/saturates separation in the same way as described in Example 12. The toluene/isooctane selectivity and flux results for this membrane are shown in FIG. 21, and its toluene/n-octane selectivity and flux results are shown in FIG. 22. In these figures, the selectivity and flux results for the polyimide/polyadipate copolymer membrane cured at 260° C. for 4 minutes are compared with those for the membrane of the same composition and thickness but cured at 260° C. for 5 minutes, which are shown in FIG. 14 (Example 12). THe latter membrane with slightly more severe curing had slightly higher selectivity but lower flux than the former with slightly less curing. These results have again reinforced our finding that increasing curing severity improves selectivity but reduces flux.

EXAMPLE 17

Thermal Stability of Copolymer Membranes

Figure 23:
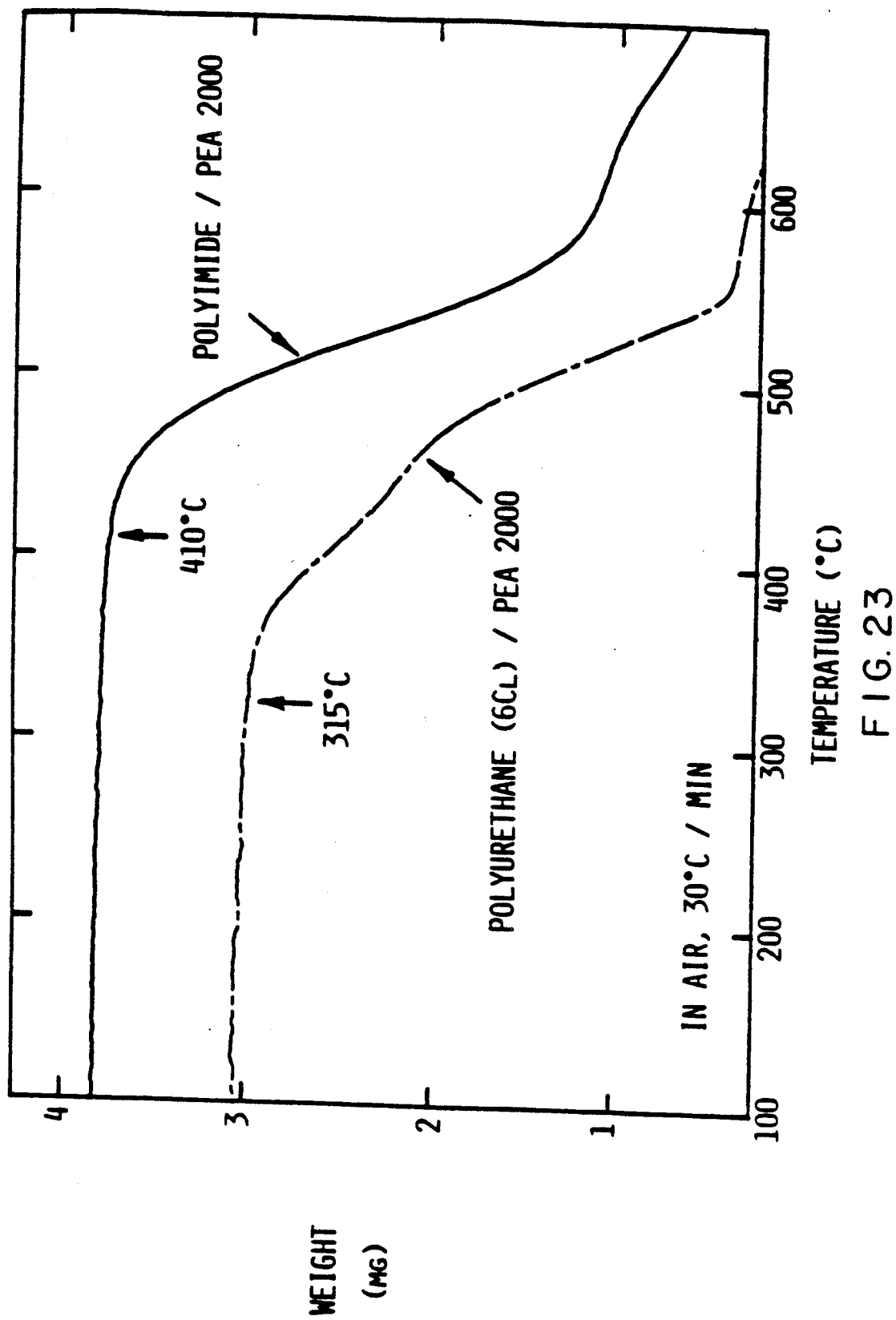
FIG. 23 shows that a polyimide copolymer of the present invention has a higher thermal decomposition temperature than a polyurethane membrane.

We characterized thermal decomposition temperatures for polyimide copolymer and chlorinated polyurethane membranes via thermogravimetric analysis. As shown in FIG. 23, the polyimide/polyadipate copolymer membrane described in Example 1 had a thermal decomposition temperature of about 410° C. in air, and the polyurethane membrane with the hard segment containing 6 chlorines shown in FIG. 3 had a thermal decomposition temperature of about 315° C. Although both polyimide copolymer and chlorinated polyurethane membranes contained the same soft segment of polyethylene adipate with a molecular weight of 2000 (PEA 2000), the polyimide copolymer membrane had a much higher thermal decomposition temperature than the chlorinated polyurethane membrane.

Figure 24:
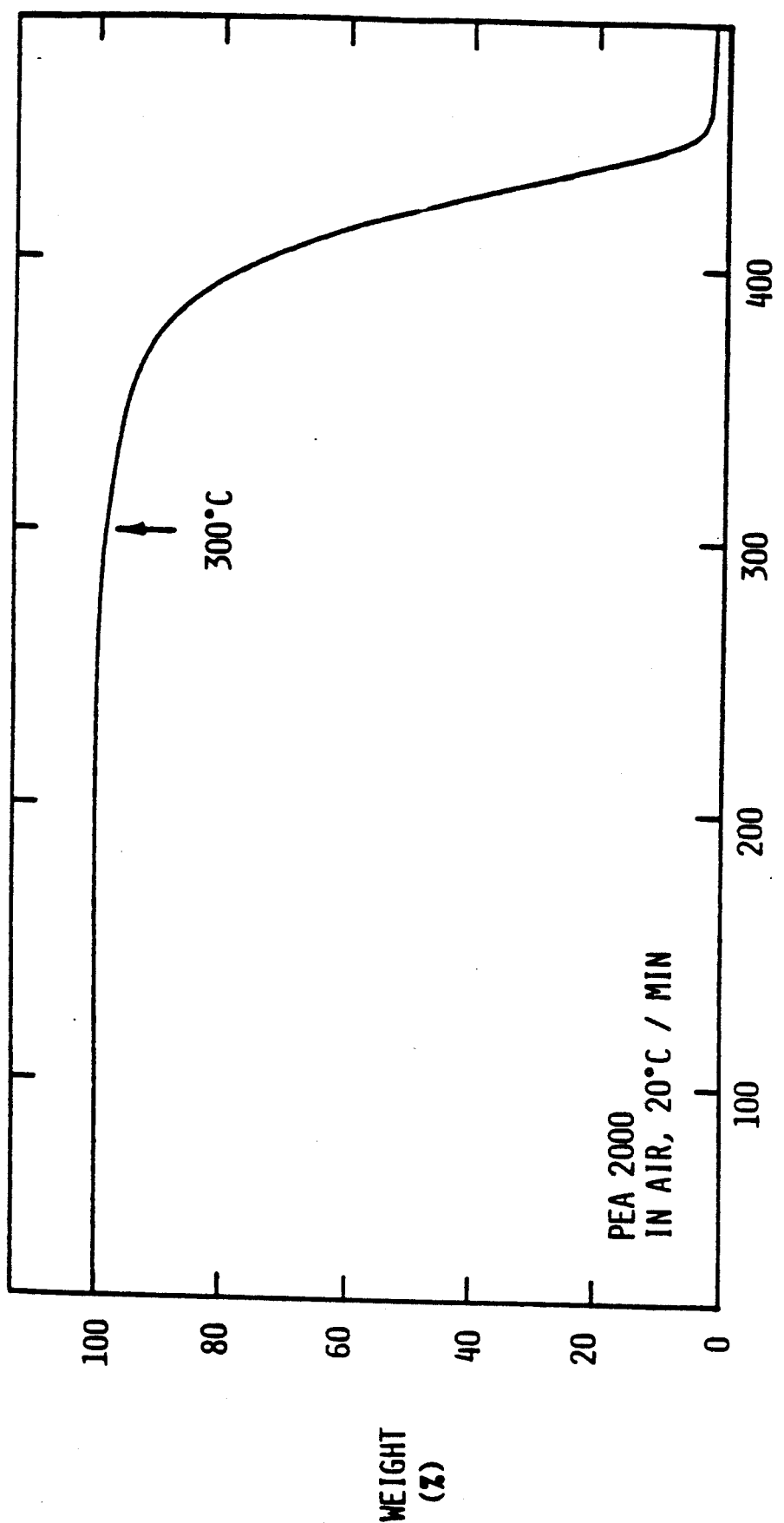
FIG. 24 shows the thermal decomposition temperature for PEA 2000 diol in air.
Figure 25:
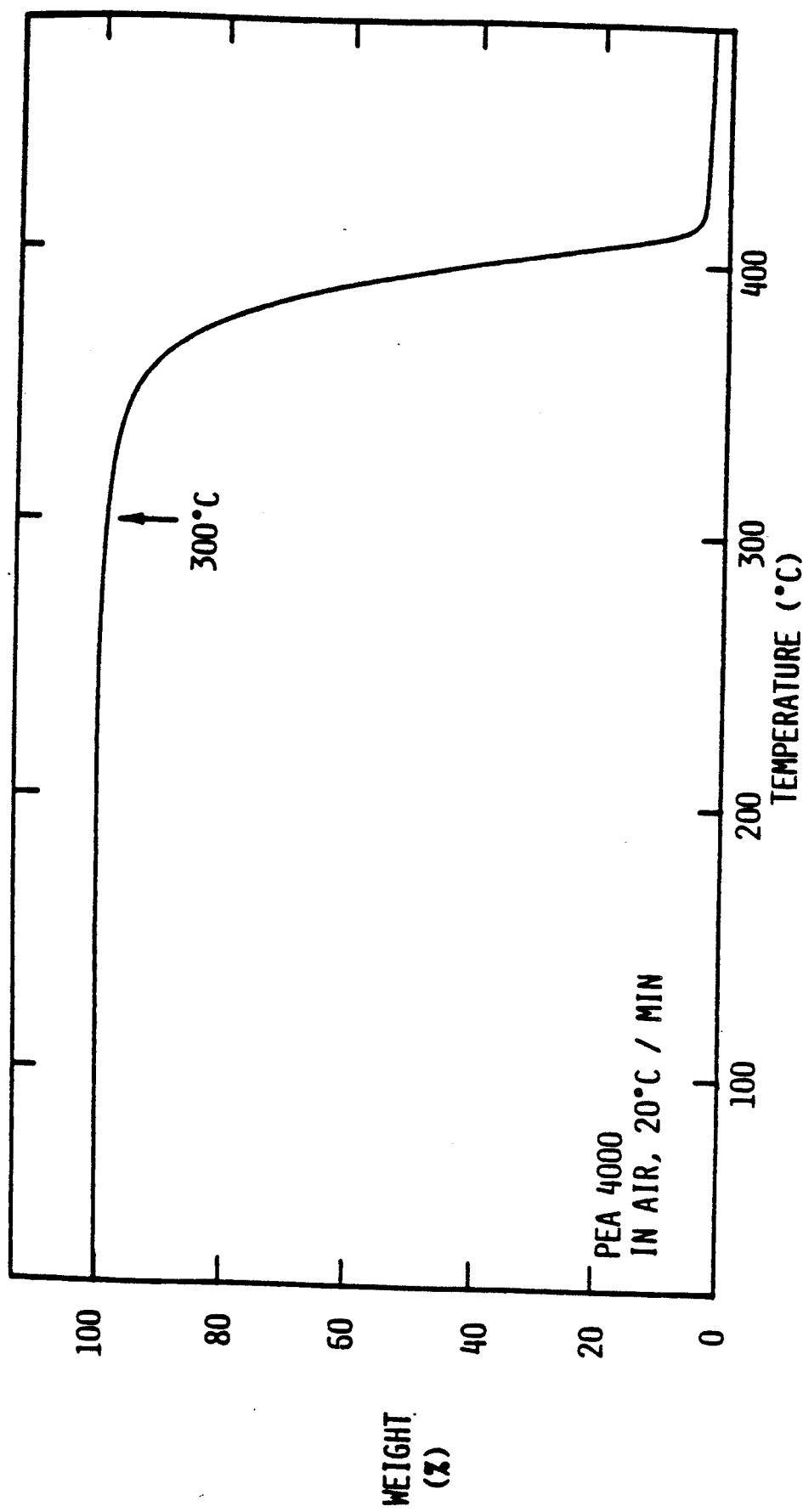
FIG. 25 shows the thermal decomposition temperature for PEA 4000 diol in air.
Figure 26:
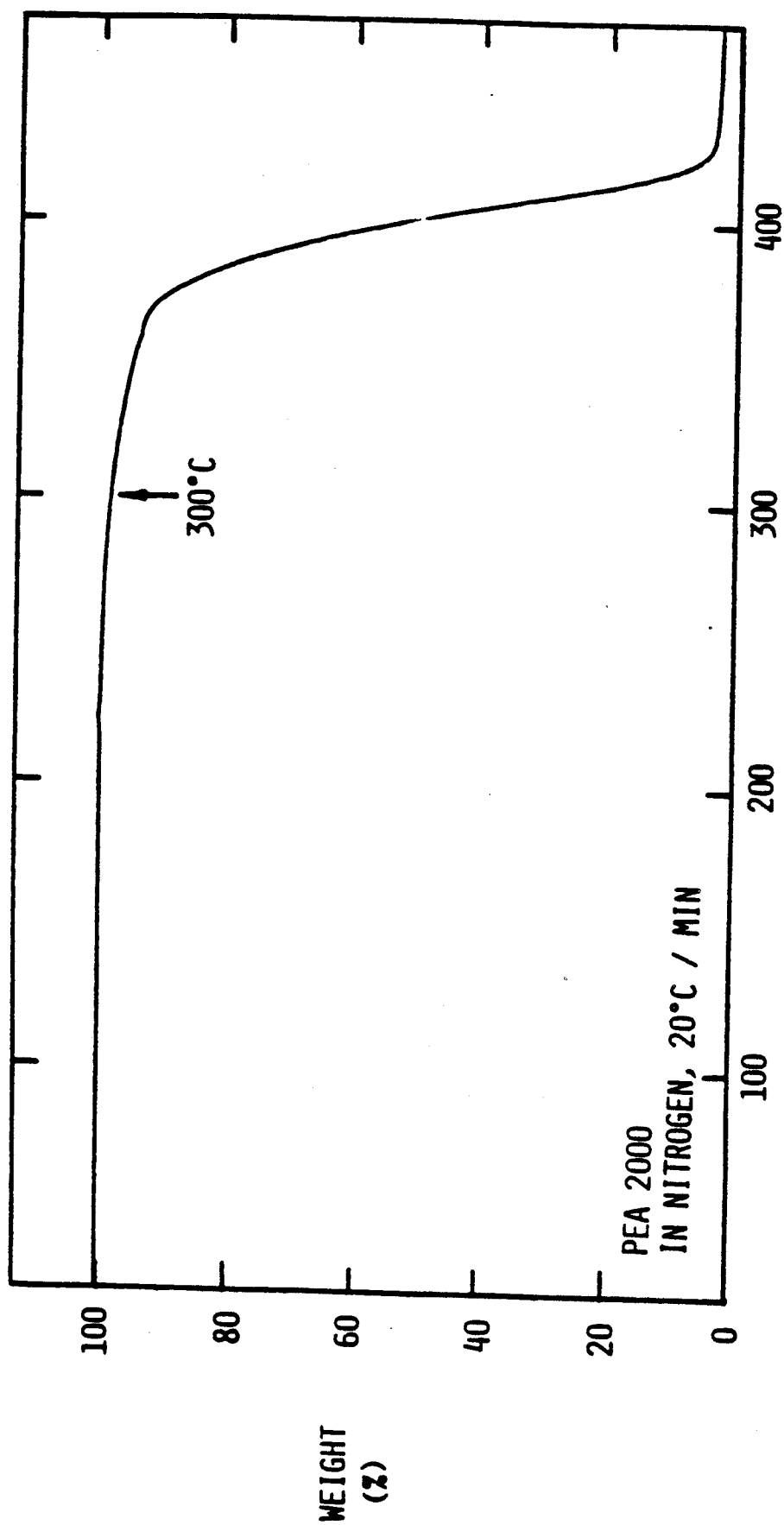
FIG. 26 shows the thermal decomposition temperature for PEA 2000 diol in nitrogen.
Figure 27:
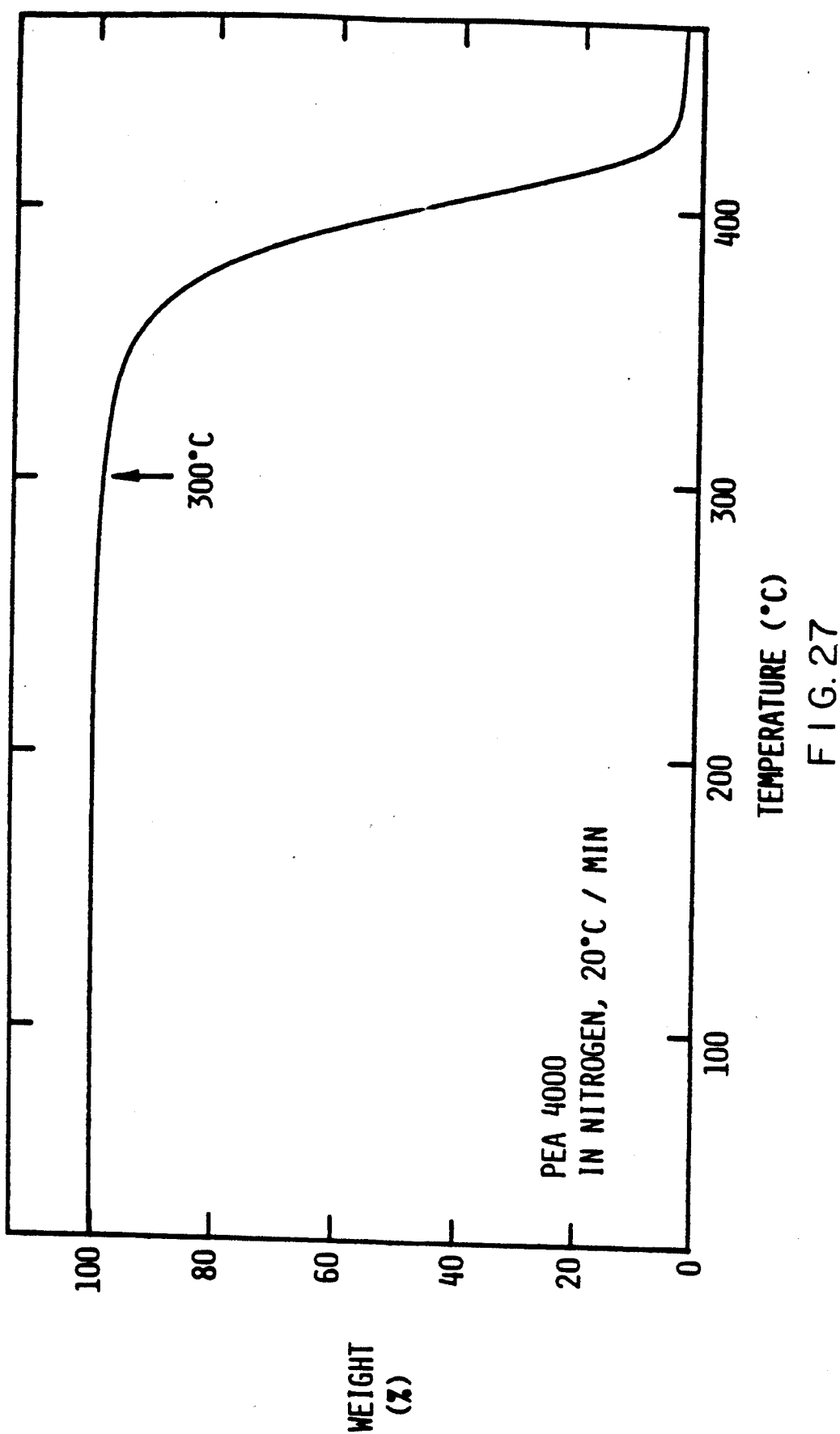
FIG. 27 shows the thermal decomposition temperature for PEA 4000 diol in nitrogen.

We also characterized thermal decomposition temperatures for polyethylene adipate diols with the molecular weights of 2000 and 4000 (PEA 2000 and PEA 4000) in air and nitrogen. FIGS. 24 and 25 show the thermal decomposition temperatures for PEA 2000 and PEA 4000 in air, respectively, and FIGS. 26 and 27 give the thermal decomposition temperatures for PEA 2000 and PEA 4000 in nitrogen, respectively. As shown in these figures, the effects of PEA molecular weight and environment (air or nitrogen) on the thermal decomposition temperature of PEA diol were insignificant. The thermal decomposition temperature for the PEA diols was about 300° C.

From the results discussed above, the thermal decomposition temperature for the polyimide/polyadipate copolymer membrane was much higher (about 100° C.) than those for the chlorinated polyurethane membrane (with the same polyadipate soft segment) and the polyadipate diol. This suggested that the decomposition temperature was affected by the hard segment. The decomposition temperature for the polyadipate diol may be influenced by its terminal hydroxyl groups. The urethane linkage between the hard and soft segments in the polyurethane membrane is less thermally stable than the ester linkage between the hard and soft segments and the imide linkages of the hard segment in the polyimide copolymer membrane.

Figure 28:
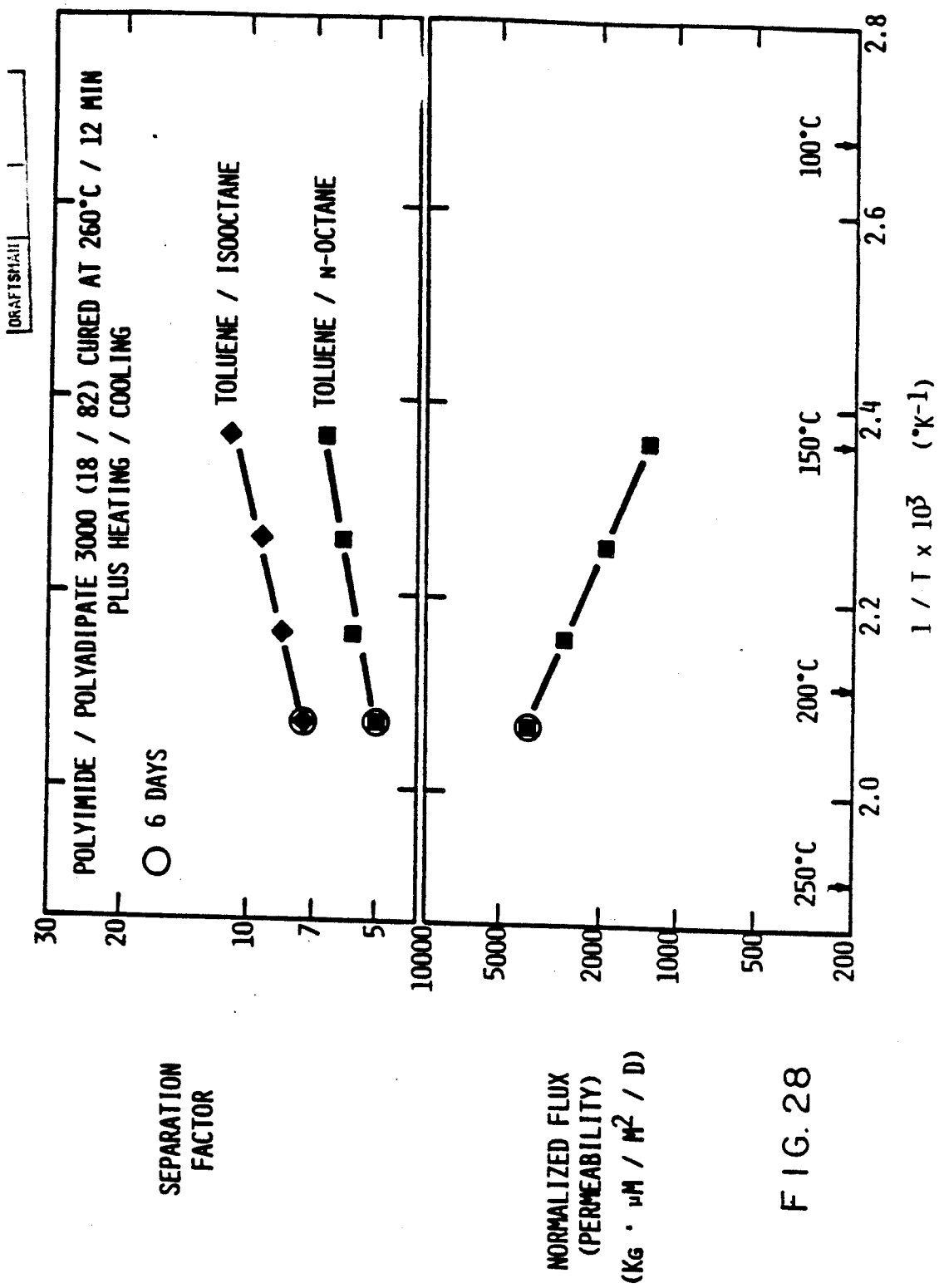
FIG. 28 shows that a polyimide copolymer of the present invention has stable selectivity and permeability (flux) for at least 6 days at 210° C.

Polyimide copolymer membranes had a temperature stability of about 210° C. in pervaporation with the feed mixture described above. FIG. 28 shows that the polyimide copolymer membrane with the soft segment of PEA 3000 described in Example 11 (FIG. 13) had stable toluene/isooctane and toluene/n-octane separation factors and flux for at least 6 days at 210° C. in pervaporation with the feed mixture. The membrane was evaluated at 150°, 170°, 190° and 210° C. for one day at each temperature. Then, the membrane was kept in the pervaporation apparatus at 210° C. for 6 days. As shown in this figure, the selectivity and flux after 6 days at 210° C. were about the same as those obtained initially at 210° C. The temperature stability of the polyimide copolymer membranes (about 210° C.) was much higher than that of about 170° C. for the chlorinated polyurethane membrane (6 Cl), which had the highest stability among the polyurethane membranes investigated.

What is claimed is:

1. A copolymer composition of matter comprising a hard segment having a glass transition temperature (Tg) of greater than 130° C. and a soft segment having a Tg less than the Tg of the hard segment, having properties for enabling separations of aromatics from saturates when used in a membrane.

2. A copolymer composition of matter of claim 1 comprising the hard segment of a polyimide and the soft segment of an oligomeric aliphatic polyester, wherein said polyimide is derived from a dianhydride having between 8 and 20 carbons and a diamine having between 2 and 30 carbons, and said oligomeric aliphatic polyester is a polyadipate, a polysuccinate, a polymalonate, a polyoxalate or a polyglutarate 3. The composition of claim 2 wherein said dianhydride is an aromatic compound 4. The composition of claim 2 wherein said diamine is selected from the group consisting of phenylene diamine, methylene dianiline (MDA), methylene di-o-chloroaniline (MOCA), methylene bis(dichloroaniline) (tetrachloro MDA), methylene dicyclohexylamine ($H_{12}$-MDA), methylene dichlorocyclohexylamine ($H_{12}$-MOCA), methylene bis(dichlorocyclohexylamine) (tetrachloro $H_{12}$-MDA), 4,4'-(hexafluoroisopropylidene)-bisaniline (6F diamine), 3,3'-diaminophenyl sulfone (3,3'DAPSON), 4,4'-diaminophenyl sulfone (4,4'DAPSON), 4,4'-dimethyl-3,3'-diaminophenyl sulfone (4,4'-dimethyl-3,3'DAPSON), 2,4-diamino cumene, methyl bis(di-o-toluidine), oxydianiline (ODA), bisaniline A, bisaniline M, bisaniline P, thiodianiline, 2,2-bis[4(4-aminophenoxy) phenyl] propane (BAPP), bis[4-(4aminophenoxy) phenyl] sulfone (BAPS), 4,4'-bis(4-aminophenoxy) biphenyl (BAPB), 1,4'-bis(4-aminophenoxy) benzene (TPE-Q), and 1,3-bis(4-aminophenoxy) benzene (TPE-R).

5. The composition of claim 3 wherein said aromatic compound is selected from the group consisting of pyromellitic dianhydride, 3,3',4,4'-benzophenone tetracarboxylic dianhydride, 4,4'-(hexafluoroisopropylidene)-bis(phthalic anhydride), 4,4'-oxydiphthalic anhydride, diphenylsulfone-3,3',4,4'-tetracarboxylic dianhydride, and 3,3',4,4'-biphenyl-tetracarboxylic dianhydride.

6. The composition of claim 2 wherein said polyester is polyethylene adipate.

7. The composition of claim 2 wherein said polyester is polyethylene succinate.

8. The composition of claim 2 wherein said diamine is methylene di-o-chloroaniline.

9. A copolymer composition of matter comprising the hard segment of a polyimide and the soft segment of an oligomeric aliphatic polyester, wherein said polyimide is derived from a dianhydride having between 8 and 20 carbons and a diamine having between 2 and 30 carbons, and said oligomeric aliphatic polyester is a polyadipate, a polysuccinate, a polymalonate, a polyoxalate or a polyglutarate.

10. The composition of claim 9 wherein said dianhydride is an aromatic compound.

11. The composition of claim 10 wherein said aromatic compound is selected from the group consisting of pyromellitic dianhydride, 3,3',4,4'-benzophenone tetracarboxylic dianhydride, 4,4'-(hexafluoroisopropylidene)-bis(phthalic anhydride), 4,4'-oxyphthalic anhydride, diphenylsulfone-3,3',4,4'-tetracarboxylic dianhydride, and 3,3',4,4'-tetracarboxylic dianhydride, and 3,3',4,4'-tetracarboxylic dianhydride, and 3,3',4,4'-biphenyl-tetracarboxylic dianhydride.

12. The composition of claim 9 wherein said diamine is selected from the group consisting of phenylene diamine, methylene dianiline (MDA), methylene di-o-chloroaniline (MOCA), methylene bis-(dichloroaniline) (tetrachloro MDA), methylene dicyclohexylamine ($H_{12}$-MDA), methylene dichlorocyclohexylamine ($H_{12}$MDA), methylene bis(dichlorocyclohexylamine) (tetrachloro $H_{12}$-MDA), 4,4'-(hexafluoroisopropylidene)-bisaniline (6F diamine), 3,3'-diaminophenyl sulfone (3,3'DAPSON), 4,4'-diaminophenyl sulfone (4,4'DAPSON), 4,4'-dimethyl-3,3'-diaminophenyl sulfone (4,4'-dimethyl-3,3'DAPSON), 2,4-diamino cumene, methyl bis(di-o-toluidine), oxydianiline (ODA), bisaniline A, bisaniline M, bisaniline P, thiodianiline, 2,2-bis propane (BAPP), bis sulfone (BAPS), 4,4'-bis(4- aminophenoxy) biphenyl (BAPB), 1,4'-bis(4-aminophenoxy) benzene (TPE-Q), and 1,3-bis(4-aminophenoxy) benzene (TPE-R).

13. The composition of claim 9 wherein said polyester is polyethylene adipate.

14. The composition of claim 9 wherein said polyester is polyethylene succinate.

15. The composition of claim 9 wherein said diamine is methylene di-o-chloroaniline.

* * * * *